United States Patent [19]

Kennis et al.

[11] Patent Number: 4,533,665

[45] Date of Patent: Aug. 6, 1985

[54] [[BIS(ARYL)METHYLENE]-1-PIPERIDINYL-]ALKYL-PYRIMIDINONES

[75] Inventors: Ludo E. J. Kennis, Turnhout; Jan Vandenberk, Beerse; Josephus C. Mertens, Oud-Turnhout, all of Belgium

[73] Assignee: Janssen Pharmaceutica, Beerse, Belgium

[21] Appl. No.: 655,136

[22] Filed: Sep. 27, 1984

Related U.S. Application Data

[60] Division of Ser. No. 517,612, Jul. 27, 1983, Pat. No. 4,485,107, which is a continuation-in-part of Ser. No. 438,079, Nov. 1, 1982, abandoned.

[51] Int. Cl.$^3$ ............... C07D 513/04; A61K 31/505
[52] U.S. Cl. .................................. 514/258; 544/278
[58] Field of Search .................... 544/278; 424/251

[56] References Cited

U.S. PATENT DOCUMENTS 4,485,107  11/1984  Kennis et al. ..................... 544/278

FOREIGN PATENT DOCUMENTS 0070053  1/1983  European Pat. Off. ............ 544/278

Primary Examiner—Donald G. Daus
Assistant Examiner—S. A. Gibson
Attorney, Agent, or Firm—Geoffrey G. Dellenbaugh

[57]  ABSTRACT

Novel [[bis(aryl)methylene]-1-piperidinyl]alkyl-pyrimidinones, wherein the pyrimidinone-ring is embraced within a bicyclic system, being useful compounds in the treatment of psychosomatic disorders.

9 Claims, No Drawings

[[BIS(ARYL)METHYLENE]-1-PIPERIDINYL]ALKYL-PYRIMIDINONES

CROSS-REFERENCE TO RELATED APPLICATIONS

This application is a divisional of our co-pending application Ser. No. 517,612, filed July 27, 1983 now U.S. Pat. No. 4,485,107 which in turn is a continuation in part of our application Ser. No. 438,079, filed Nov. 1, 1982, now abandoned.

BACKGROUND OF THE INVENTION 3-(1-Piperidinylalkyl)-4H-pyrido[1,2-a]pyrimidin-4-ones having the piperidine-ring substituted with an arylcarbonyl radical or a functional derivative thereof are described in U.S. Pat. No. 4,342,870.

(1-Piperidinyl)alkyl-5H-thiazolo-[3,2-a]pyrimidin-5-ones, -2H, 6H-pyrimido[2,1-b][1,3]thiazin-6-ones and -5H-thiazolo[3,2-a]-pyrimidin-5-ones having the piperidine-ring substituted with an arylcarbonyl radical or a functional derivative thereof are described in U.S. patent application Ser. No. 370,653 filed Apr. 21, 1982.

[[Bis(aryl)methylene]-1-piperidinyl]alkanone derivatives are described in U.S. Pat. No. 3,862,173.

The compounds of the present invention differ from the hereinabove-cited compounds by the substitution of the piperidine-ring or by the substitution of the [[bis-(aryl)methylene]-1-piperidinyl]alkane moiety with a bicyclic pyrimidinone radical and by their useful serotonine-antagonistic properties making those compounds attractive in the treatment of diseases wherein serotonine has a non-neglectible influence such as, for example, in the treatment of psychosomatic disorders.

DESCRIPTION OF THE PREFERRED EMBODIMENTS

The present invention is concerned with a novel series of (1-piperidinylalkyl)pyrimidinone derivatives which are structurally represented by the formula

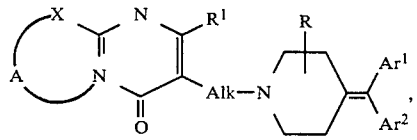

(I)

the possible stereochemically isomeric forms and the pharmaceutically acceptable acid-addition salts thereof, wherein:

R is hydrogen, hydroxy or lower alkyloxy;

$R^1$ is a member selected from the group consisting of hydrogen and lower alkyl;

Alk is a lower alkanediyl radical;

X is a member selected from the group consisting of —S—, —CH$_2$— and —C($R^2$)=C($R^3$)—, said $R^2$ and $R^3$ being each independently hydrogen or lower alkyl;

A is a bivalent radical having the formula —CH$_2$—CH$_2$—, —CH$_2$—CH$_2$—CH$_2$— or

wherein $R^4$ and $R^5$ are each independently selected from the group consisting of hydrogen, halo, amino and lower alkyl; and $Ar^1$ and $Ar^2$ are each independently selected from the group consisting of pyridinyl, thienyl and phenyl, being optionally substituted with halo, hydroxy, lower alkyloxy, lower alkyl and trifluoromethyl.

In the foregoing definitions the term halo is generic to fluoro, chloro, bromo and iodo; "lower alkyl" is meant to include straight and branched saturated hydrocarbon radicals, having from 1 to 6 carbon atoms, such as, for example, methyl, ethyl, 1-methylethyl, 1,1-dimethylethyl, propyl, butyl, pentyl, hexyl and the like; and "lower alkanediyl" is meant to include bivalent straight or branch chained alkanediyl radicals having from 1 to 6 carbon atoms.

Preferred compounds within the scope of the present invention are those wherein Alk is an 1,2-ethanediyl radical.

The most preferred compounds within the scope of the present invention is 6-[2-[4-[bis(4-fluorophenyl)methylene]-1-piperidinyl]ethyl]-7-methyl-5H-thiazolo[3,2-a]pyrimidin-5-one or a pharmaceutically acceptable acid addition salt thereof.

The compounds of formula (I) can generally be prepared by reacting an appropriate reactive ester of formula (II) with an appropriately substituted piperidine of formula (III). In the reactive ester (II) A, X, $R^1$ and Alk are as previously described and W represents a reactive leaving group such as, for example, halo, particularly, chloro, bromo and iodo, or a sulfonyloxy group, e.g., methylsulfonyloxy, 4-methylphenylsulfonyloxy and the like.

In the piperidine (III) R, $Ar^1$ and $Ar^2$ are as previously described.

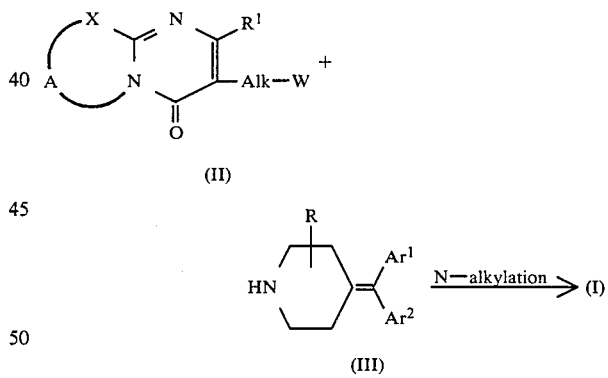

The foregoing reaction may be carried out following standard N-alkylating procedures. Said reaction is preferably carried out in an appropriate reaction-inert solvent such as, for example, a lower alkanol, e.g., methanol, ethanol, propanol, butanol and the like alkanols; an aromatic hydrocarbon, e.g., benzene, methylbenzene, dimethylbenzene, and the like; an ether, e.g., 1,4-dioxane, 1,1'-oxybispropane and the like; a ketone, e.g., 4-methyl-2-pentanone; N,N-dimethylformamide; nitrobenzene; and the like. The addition of an appropriate base such as, for example, an alkali or earth alkaline metal carbonate or hydrogen carbonate, may be utilized to pick up the acid which is liberated during the course of the reaction. A small amount of an appropriate metal iodide, e.g., sodium or potassium iodide may be added as a reaction promotor. Somewhat elevated temperatures are appropriate to enhance the rate of the reaction and preferably the reaction is carried out at the reflux temperature of the reaction mixture.

The compounds of formula (I) can also be prepared following art-known cyclizing procedures for preparing pyrimidin-4-ones such as, for example, by reacting an amine of formula (IV) with a cyclizing agent of formula (V) or by cyclizing a reagent of formula (VI) with an amine of formula (VII).

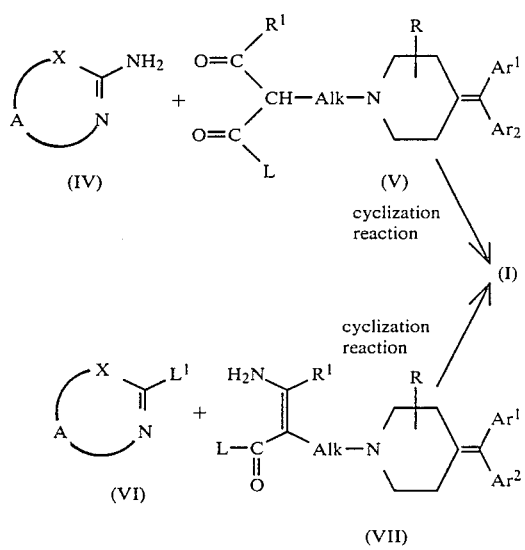

In the formulas (IV), (V), (VI) and (VII) A, X, R, $R^1$, Alk, $Ar^1$ and $Ar^2$ are as previously described and L and $L^1$ represent each independently an appropriate leaving group such as, for example, lower alkyloxy, hydroxy, halo, amino, mono- and di(lower alkyl)amino and the like.

Additionally, the compounds of formula (I) can also be prepared by cyclizing an intermediate of formula (VII) with an isothiocyanate of formula (VIII).

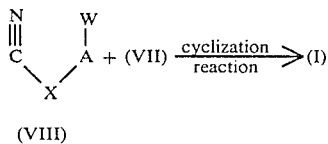

The foregoing cyclization reaction may be carried out following the same procedure as described for the preparation of (I) starting from (IV) and (V).

The compounds of formula (I) wherein X is S, said compounds being represented by the formula (I-a), can also be prepared by cyclizing a 2-mercaptopyrimidinone of formula (IX) with a reagent of formula (X).

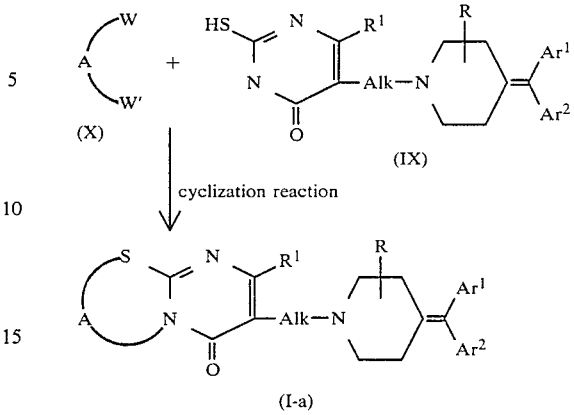

In (X) W' has the same meaning as previously described for W.

The compounds of formula (I-a) wherein A is $$-\underset{\underset{R^4}{|}}{C}=\underset{\underset{R^5}{|}}{C}-,$$

said compounds being represented by the formula (I-a-1), can also be prepared by cyclizing a 2-mercaptopyrimidinone of formula (IX) with a reagent of formula (XI).

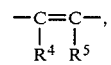

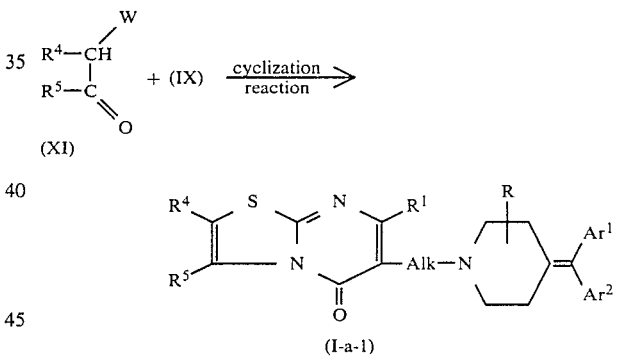

The cyclization reaction wherein the compounds of formula (I) are prepared starting from (IV) and (V), (VI) and (VII), (VIII) and (VII), (X) and (IX) or (XI) and (IX) may generally be carried out by stirring the reactants together, if desired, in the presence of a suitable reaction-inert solvent such as, for example, an aliphatic-, alicyclic- or aromatic hydrocarbon, e.g., hexane, cyclohexane, benzene and the like; pyridine; N,N-dimethylformamide and the like amides. Elevated temperatures may be appropriate to enhance the reaction-rate. In some cases it may be preferable to carry out the reaction at the reflux temperature of the reaction mixture.

The compounds of formula (I) may also be converted into each other following art-known functional group-transformation procedures.

For example the compounds of formula (I) wherein $Ar^1$ and/or $Ar^2$ is/are phenyl substituted by hydroxy can be converted into the corresponding compounds of formula (I) wherein $Ar^1$ and/or $Ar^2$ is/are phenyl substituted by lower alkyloxy following art-known O-alkylating procedures.

For example, compounds of formula (I) wherein Ar¹ is phenyl substituted by hydroxy, said compounds being represented by the formula (I-b), can be converted into compounds of formula (I) wherein Ar¹ is phenyl substituted by lower alkyloxy, said compounds being represented by the formula (I-c), by reacting the former with an appropriate lower alkylhalide (XII).

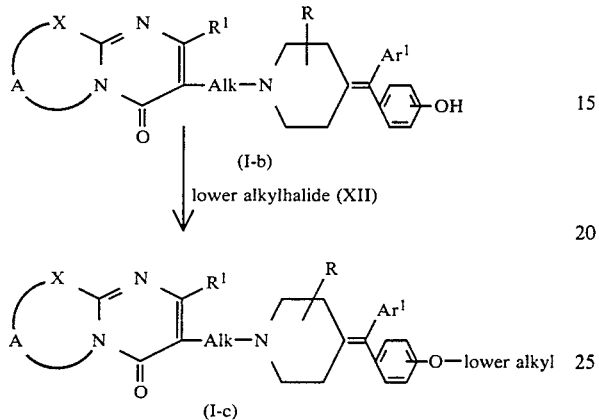

Said O-alkylation reaction can conveniently be conducted in a suitable solvent in the presence of an appropriate base, e.g., sodium hydride and the like.

The compounds of formula (I) have basic properties and, consequently, they may be converted to their therapeutically active non-toxic acid addition salt forms by treatment with appropriate acids, such as, for example, inorganic acids, such as hydrohalic acid, e.g. hydrochloric, hydrobromic and the like, and sulfuric acid, nitric acid, phosphoric acid and the like; or organic acids, such as, for exmple, acetic, propanoic, hydroxyacetic, 2-hydroxypropanoic, 2-oxopropanoic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids.

Conversely the salt form can be converted by treatment with alkali into the free base form.

It is obvious from formula (I) that the compounds of the present invention wherein Alk represents an asymmetrically branched lower alkanediyl radical may exist under different stereochemically isomeric forms.

This chiral center may be present in a R- and a S-configuration, this R- and S-notation being in correspondence with the rules described in R. S. Cahn, C. Ingold and V. Prelog in Angew. Chem. Int. Ed. Engl., 5, 385, 511 (1966). Consequently, the compounds of formula (I) may be present in two different enantiomeric forms, which may be separated from each other, for example, by converting the mixture of enantiomers into the acid addition salt form thereof with an optically active acid, separating the diastereomeric salts, e.g., by selective crystallization, and liberating the pure enantiomers by treatment with alkali.

Pure stereochemically isomeric forms may also be derived from the corresponding pure stereochemically isomeric forms of the appropriate starting materials, provided that the reaction occurs stereospecifically or highly stereoselectively.

Stereochemically isomeric forms of the compounds of formula (I) are naturally intended to be embraced within the scope of the invention.

A number of the intermediates and starting materials used in the foregoing preparations are known compounds, others may be prepared according to art-known methodologies of preparing similar compounds and for some of them synthetic methods are presented hereinafter.

The intermediates of formula (II) can be prepared by converting the hydroxyl function of the corresponding alcohols (XIII) into a reactive leaving group, e.g., by reacting the alcohols (XIII) with thionyl chloride, sulfuryl chloride, phosphor pentabromide, phosphoryl chloride, methanesulfonyl chloride, 4-methylbenzenesulfonyl chloride and the like.

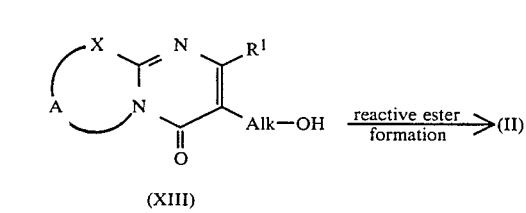

The alcohols (XIII), used as starting materials herein, may be prepared following cyclization procedures which are analogous to those described hereinabove for the preparation of compounds of the formula (I). Said cyclization reactions starting from (IV) and (XIV), from (VI) and (XV) and from (VIII) and (XV) are represented in Scheme 1.

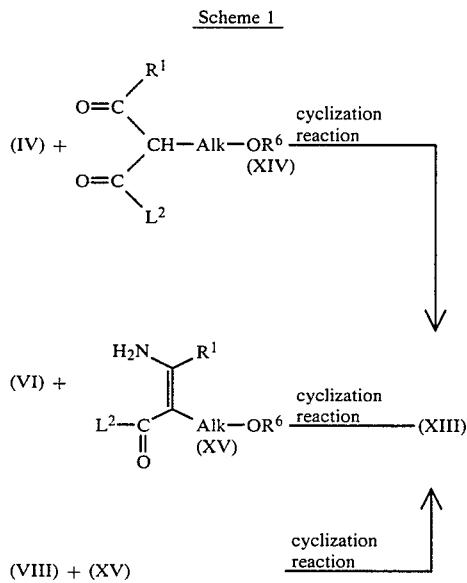

As used in Scheme 1 R⁶ may be hydrogen and L² may have the same meaning as described hereinabove for L and, additionally, R⁶ and L², when taken together, may represent a direct bond.

The alcohols (XIII) wherein X is S, (XIII-a), may be prepared by the cyclization reaction of (X) with (XVI) following the same procedure as described hereinabove for the preparation of (I-a) starting from (X) and (IX).

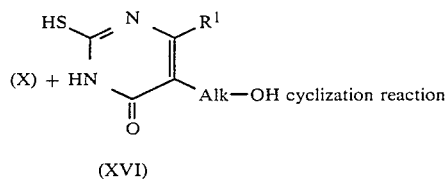

(XVI)

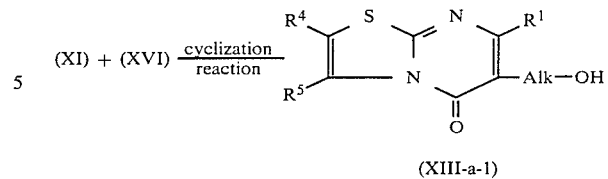

(XIII-a-1)

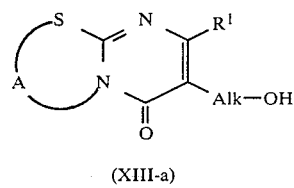

(XIII-a)

The alcohols (XIII-a) wherein A is

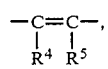

(XIII-a-1), can be prepared by the cyclization reaction of (XI) with (XVI) following the same procedure as described hereinabove for the preparation of (I-a-1) starting from (XI) and (IX).

In some cases it may be advantageous to conduct the cyclization reaction and the reactive ester formation reaction simultaneously.

The intermediates of formula (II) wherein W is halo, said intermediates being represented by the formula

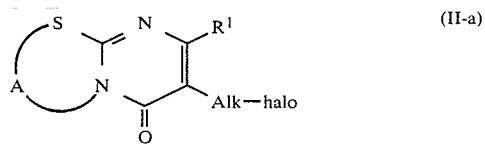

can also be derived from (IV) and (XV), or (VI) and (XV), or (VIII) and (XV), or (X) and (XIV) in a direct way, by stirring and, if desired, heating the reactants in a suitable solvent in the presence of a suitable halogenating agent, e.g., phosphoryl chloride, thionyl chloride, phosphorpentabromide and the like. Optionally, said cyclizing and halogenating reaction can be carried out in acidic medium, e.g., in the presence of hydrogen chloride, 4-methylphenylsulfonic acid and the like acids.

The intermediates of formula (V), (VII), (XIV) and (XV) can be derived from a compound having the formula (XVII), as shown in Scheme 2.

Scheme 2

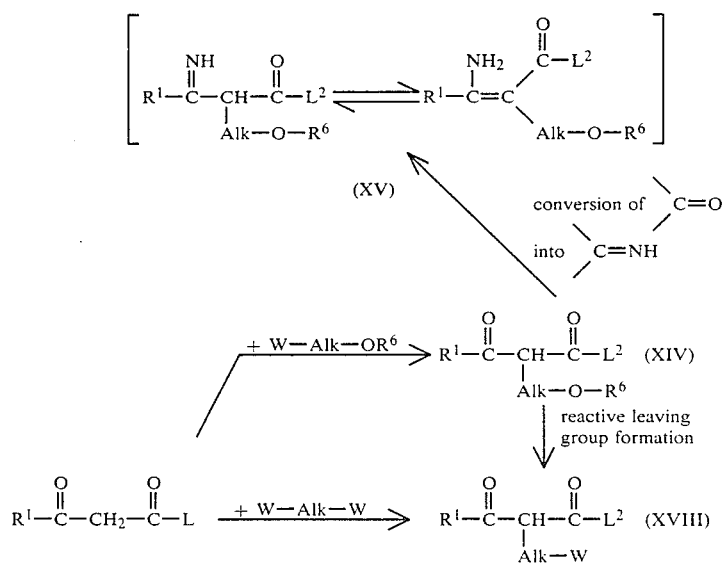

Scheme 2

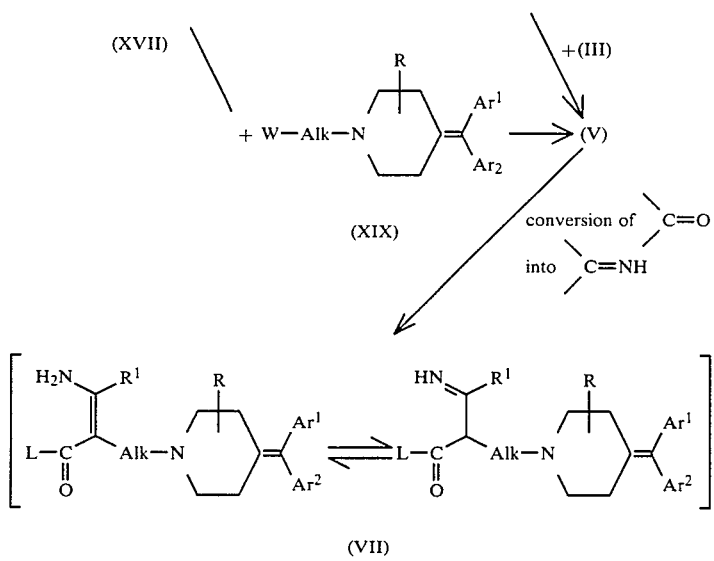

The intermediates of formula (V) can be prepared by stirring and, if desired, heating (XVII) with (XIX) in the presence of a strong base, e.g., sodium hydride, sodium methoxide and the like in a suitable solvent. The intermediates of formula (V) can also be prepared by reacting (XVII) with a reagent of formula W-Alk-W, as described for the reaction of (XVII) with (XIX) and, subsequently, reacting the thus obtained (XVIII) with (III) following art-known N-alkylating procedures.

The intermediates of formula (XVIII) may also be prepared by reacting (XVII) with a reagent of formula W-Alk-OR$^6$, as described for the reaction of (XVII) with (XIX) and, subsequently, converting the hydroxyl function in the thus obtained (XIV) into a reactive leaving group, as described hereinabove.

The intermediates of formula (XV) and the intermediates of formula (VII) can be derived from (XIV) respectively (V) by converting the carbonyl function into an imine function, which imine is in equilibrium with its tautomeric form.

The intermediates of formula (III) may be prepared by reacting a piperidine (XX) with a ketone (XXI) following art-known Grignard-reaction procedures, subsequently dehydrating the thus prepared tertiary alcohol (XXII) and eliminating the protective group P from the thus obtained unsaturated intermediate (XXIII).

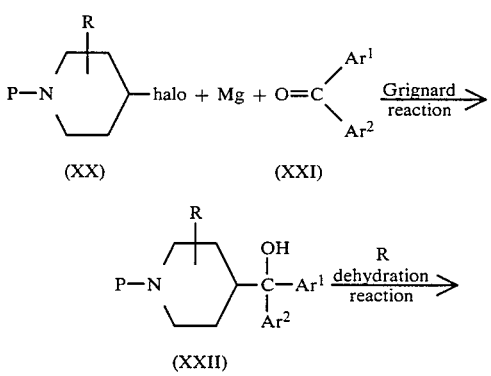

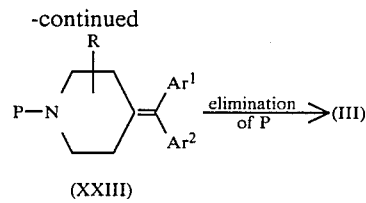

The compounds of formula (I), the possible stereochemically isomeric forms and the pharmaceutically acceptable acid addition salts thereof combine a potent serotonin antagonistic activity with a high degree of specificity for the serotonin receptors in comparison with other receptors such as, for example, dopamine-, norepinephrine- and acetylcholine receptors. Additionally, the said compounds are acetylcholine receptors. Additionally, the said compounds are binding selectively with the S$_2$-receptor, this S$_2$-notation being in correspondence with the terminology used in, for example, Molecular Pharmacology 21, 301-314 (1982).

Moreover, the compounds of the present invention are characterized by their long duration of activity.

The S$_2$-antagonistic activity of the compounds of formula (I) their possible stereochemically isomeric forms and their pharmaceutically acceptable acid addition salts is evidenced by the experimental data obtained in the caudal actery test.

ANTAGONISTIC ACTIVITY ON THE EFFECT OF SEROTONIN ON THE CAUDAL ARTERY OF THE RAT

Caudal arteries from fasted male rats (210-235 g) were used in the test. Two helical strips having a length of 5-6 cm and a width of 2 mm. were obtained from each artery and mounted vertically in a 100 ml organ bath containing an oxygenated Krebs-Henseleit solution. Submaximal contractions of the arterial strips were produced by adding single doses of serotonin (40 ng/ml) to the organ bath for 2 minutes with each time an interval of 10 minutes. The amplitude of the contraction was measured before and 5 minutes after adding the drug. After washing out, the agonist was added again three times in order to see whether the contraction was restored and normalized. Table 1 shows the $ED_{50}$-values in ng/ml for a number of compounds of formula (I) and their pharmaceutically acceptable acid addition salts in the above test. In this connection the $ED_{50}$-values are the minimal concentrations of the concerned drugs which reduce the amplitude of the contraction to at least 50% of its normal value.

TABLE 1

Structure:

$$\begin{array}{c} \text{A ring system with X, N, CH}_3\text{, (CH}_2)_n\text{-N, R, Ar}^1\text{, Ar}^2 \end{array}$$

| comp. no. | X | A | n | R | $Ar^1$ | $Ar^2$ | base or salt form | $ED_{50}$ in ng/ml |
|---|---|---|---|---|---|---|---|---|
| 112 | S | CH=C(CH₃) | 2 | H | 4-F—C₆H₄ | 4-F—C₆H₄ | base | 0.00032 |
| 1 | S | CH=CH | 2 | H | 4-F—C₆H₄ | 4-F—C₆H₄ | base | 0.00008 |
| 113 | S | CH₂—CH₂ | 2 | H | 4-F—C₆H₄ | 4-F—C₆H₄ | 2HCl | 0.00056 |
| 3 | CH₂ | CH₂—CH₂—CH₂ | 2 | H | 4-F—C₆H₄ | 4-F—C₆H₄ | base | 0.00056 |
| 114 | S | CH₂—CH₂—CH₂ | 2 | H | 4-F—C₆H₄ | 4-F—C₆H₄ | base | 0.00056 |
| 2 | CH=CH | CH=CH | 2 | H | 4-F—C₆H₄ | 4-F—C₆H₄ | 2HCl | 0.0013 |
| 137 | CH₂ | CH₂—CH₂—CH₂ | 2 | H | 4-F—C₆H₄ | C₆H₅ | 2HCl | 0.0013 |
| 115 | S | CH₂—CH₂—CH₂ | 2 | H | 4-F—C₆H₄ | C₆H₅ | 2HCl | 0.0013 |
| 116 | S | CH₂—CH₂ | 2 | H | 4-F—C₆H₄ | C₆H₅ | 2HCl.H₂O | 0.0013 |
| 117 | S | CH=C(CH₃) | 2 | H | 4-F—C₆H₄ | C₆H₅ | HCl | <0.00063 |
| 4 | S | CH=CH | 2 | H | C₆H₅ | C₆H₅ | base | 0.00016 |
| 5 | S | CH₂—CH₂ | 2 | H | 4-F—C₆H₄ | 3-Cl—C₆H₄ | base | 0.00016 |
| 6 | S | CH=CH | 2 | H | 4-F—C₆H₄ | 3-Cl—C₆H₄ | base | 0.00063 |
| 7 | S | CH=C(CH₃) | 2 | H | 4-F—C₆H₄ | 3-Cl—C₆H₄ | base | 0.00063 |
| 9 | S | CH=CH | 2 | H | 4-F—C₆H₄ | 4-Cl—C₆H₄ | base | <0.00063 |
| 11 | CH₂ | CH₂—CH₂—CH₂ | 2 | H | 4-F—C₆H₄ | 4-Cl—C₆H₄ | base | 0.00125 |
| 13 | CH=CH | CH=CH | 2 | H | 4-F—C₆H₄ | 4-Cl—C₆H₄ | base | 0.00125 |
| 105 | S | CH=C(CH₃) | 2 | H | C₆H₅ | C₆H₅ | base | 0.00032 |
| 138 | CH₂ | CH₂—CH₂—CH₂ | 2 | H | C₆H₅ | 3-CH₃—C₆H₄ | 2HCl | 0.00125 |
| 14 | S | CH=CH | 2 | H | 4-F—C₆H₄ | 3-CH₃—C₆H₄ | base | 0.00063 |
| 15 | CH=CH | CH=CH | 2 | H | 4-F—C₆H₄ | 3-CH₃—C₆H₄ | 2HCl | 0.00063 |
| 139 | S | CH=CH | 2 | H | 4-F—C₆H₄ | C₆H₅ | HCl | 0.00016 |
| 16 | CH=CH | CH=CH | 2 | H | 4-F—C₆H₄ | 3-Cl—C₆H₄ | (E)-2-butene-dioic acid | 0.00063 |
| 18 | CH=CH | CH=CH | 2 | H | C₆H₅ | C₆H₅ | base | <0.00063 |
| 104 | S | CH₂—CH₂—CH₂ | 2 | H | C₆H₅ | C₆H₅ | base | 0.00032 |
| 20 | CH=CH | CH=CH | 2 | H | 4-F—C₆H₄ | 4-OH—C₆H₄ | base | 0.00125 |
| 143 | CH=CH | CH=CH | 2 | H | 4-F—C₆H₄ | 4-OCH₃—C₆H₄ | 2HCl.H₂O | 0.00063 |
| 118 | S | CH₂—CH₂ | 2 | H | 4-F—C₆H₄ | 3-CF₃—C₆H₄ | 2HCl | 0.00125 |
| 21 | S | CH=CH | 2 | H | 4-F—C₆H₄ | 3-CF₃—C₆H₄ | 2HCl | 0.00063 |
| 119 | S | CH=C(CH₃) | 2 | H | 4-F—C₆H₄ | 3-CF₃—C₆H₄ | base | 0.00125 |
| 140 | CH₂ | CH₂—CH₂—CH₂ | 2 | H | 4-F—C₆H₄ | 3-CF₃—C₆H₄ | 2HCl | 0.00125 |
| 120 | S | CH₂—CH₂—CH₂ | 2 | H | 4-F—C₆H₄ | 3-CF₃—C₆H₄ | 2HCl | 0.00056 |
| 121 | S | CH₂—CH₂—CH₂ | 2 | H | 4-F—C₆H₄ | 3-CH₃—C₆H₄ | base | 0.0013 |
| 22 | S | CH₂—CH₂ | 2 | H | 4-F—C₆H₄ | 4-Cl—C₆H₄ | HCl.H₂O | 0.0013 |
| 23 | S | CH=C(CH₃) | 2 | H | 4-F—C₆H₄ | 4-OH—C₆H₄ | base | 0.00056 |
| 24 | S | CH=CH | 2 | H | 4-F—C₆H₄ | 4-OH—C₆H₄ | base | 0.00018 |
| 122 | S | CH=C(CH₃) | 2 | H | 4-F—C₆H₄ | 3-CH₃—C₆H₄ | base | 0.00032 |
| 25 | S | CH=CH | 2 | H | 4-F—C₆H₄ | 3-F—C₆H₄ | (E)-2-butene-dioic acid | 0.00014 |
| 26 | S | CH=CH | 2 | H | 4-CH₃—C₆H₄ | 4-CH₃—C₆H₄ | base | 0.00056 |
| 142 | S | CH=C(CH₃) | 2 | H | 4-F—C₆H₄ | 4-OCH₃—C₆H₄ | base | 0.00056 |
| 123 | S | CH₂—CH₂—CH₂ | 2 | H | 4-F—C₆H₄ | 3-CH₃—C₆H₄ | 2HCl | 0.00032 |
| 27 | S | CH=C(CH₃) | 2 | H | 4-F—C₆H₄ | 3-F—C₆H₄ | (E)-2-butene-dioic acid | 0.00032 |
| 28 | S | CH₂—CH₂ | 2 | H | 4-F—C₆H₄ | 3-F—C₆H₄ | (E)-2-butene-dioic acid | 0.00056 |
| 29 | S | CH₂—CH₂—CH₂ | 2 | H | 4-F—C₆H₄ | 4-F—C₆H₄ | (E)-2-butene-dioic acid | 0.00032 |
| 30 | CH₂ | CH₂—CH₂—CH₂ | 2 | H | 4-F—C₆H₄ | 3-F—C₆H₄ | (E)-2-butene-dioic acid | 0.00056 |
| 31 | CH=CH | CH=CH | 2 | H | 4-F—C₆H₄ | 3-CF₃—C₆H₄ | 2HCl | 0.0025 |
| 32 | S | CH=C(CH₃) | 2 | H | 4-F—C₆H₄ | 4-Br—C₆H₄ | base | 0.0013 |
| 33 | S | CH₂—CH₂—CH₂ | 2 | H | 4-F—C₆H₄ | 4-Br—C₆H₄ | base | 0.0028 |
| 34 | S | CH=CH | 2 | H | 4-F—C₆H₄ | 4-Br—C₆H₄ | base | 0.00056 |
| 35 | CH₂ | CH₂—CH₂—CH₂ | 2 | H | 4-F—C₆H₄ | 4-Br—C₆H₄ | base | 0.00071 |
| 36 | CH=CH | CH=CH | 2 | H | 4-F—C₆H₄ | 3-F—C₆H₄ | (E)-2-butene-dioic acid | 0.00032 |
| 37 | S | CH₂—CH₂—CH₂ | 2 | H | 4-F—C₆H₄ | 4-OH—C₆H₄ | base | 0.0013 |
| 144 | S | CH=CH | 2 | H | 4-F—C₆H₄ | 4-OCH₃—C₆H₄ | HCl | 0.00056 |
| 38 | S | CH=C(CH₃) | 2 | H | 4-F—C₆H₄ | 4-CH₃—C₆H₄ | base | 0.00032 |
| 39 | CH₂ | CH₂—CH₂—CH₂ | 2 | H | 4-F—C₆H₄ | 4-OH—C₆H₄ | base | 0.00063 |
| 40 | S | CH₂—CH₂—CH₂ | 2 | H | 4-F—C₆H₄ | 4-CH₃—C₆H₄ | (E)-2-butene-dioic | 0.00056 |
| 107 | S | CH₂—CH₂ | 2 | H | C₆H₅ | C₆H₅ | 2HCl | 0.00056 |
| 41 | CH=CH | CH=CH | 2 | H | 4-F—C₆H₄ | 4-CH₃—C₆H₄ | (E)-2-butene-dioic | 0.00032 |

TABLE 1-continued

| comp. no. | X | A | n | R | Ar¹ | Ar² | base or salt form | ED$_{50}$ in ng/ml |
|---|---|---|---|---|---|---|---|---|
| 145 | S | CH$_2$—CH$_2$—CH$_2$ | 2 | H | 4-F—C$_6$H$_4$ | 4-OCH$_3$—C$_6$H$_4$ | 2HCl | 0.0013 |
| 108 | S | CH$_2$—CH$_2$—CH$_2$ | 2 | H | 4-CH$_3$—C$_6$H$_4$ | 4-CH$_3$—C$_6$H$_4$ | base | 0.0013 |
| 42 | CH$_2$ | CH$_2$—CH$_2$—CH$_2$ | 2 | H | 4-F—C$_6$H$_4$ | 4-CH$_3$—C$_6$H$_4$ | 2HCl | 0.0022 |
| 43 | CH=CH | CH=CH | 2 | H | 4-CH$_3$—C$_6$H$_4$ | 4-CH$_3$—C$_6$H$_4$ | 2HCl | 0.00071 |
| 44 | S | CH$_2$—CH$_2$ | 2 | H | 4-F—C$_6$H$_4$ | 4-Br—C$_6$H$_4$ | HCl | 0.00056 |
| 146 | CH$_2$ | CH$_2$—CH$_2$—CH$_2$ | 2 | H | 4-F—C$_6$H$_4$ | 4-OCH$_3$—C$_6$H$_4$ | 2HCl | 0.0013 |
| 45 | CH=CH | CH=CH | 2 | H | 4-F—C$_6$H$_4$ | 4-Br—C$_6$H$_4$ | base | 0.0013 |
| 46 | CH$_2$ | CH$_2$—CH$_2$—CH$_2$ | 2 | H | 4-F—C$_6$H$_4$ | 4-CH$_3$—C$_6$H$_4$ | (E)-2-butene-dioic | 0.0013 |
| 47 | S | CH$_2$—CH$_2$ | 2 |   | 4-F—C$_6$H$_4$ | 4-CH$_3$—C$_6$H$_4$ | (E)-2-butene-dioic | 0.00032 |
| 48 | S | CH=CH | 2 | H | 4-Cl—C$_6$H$_4$ | 4-Cl—C$_6$H$_4$ | base | 0.0022 |
| 49 | S | CH=CH | 2 | H | 4-F—C$_6$H$_4$ | 4-CH$_3$—C$_6$H$_4$ | (E)-2-butene-dioic | 0.00032 |
| 110 | S | CH$_2$—CH$_2$ | 2 | H | 4-Cl—C$_6$H$_4$ | 4-Cl—C$_6$H$_4$ | base | 0.0013 |
| 50 | CH=CH | C(CH$_3$)=CH | 2 | H | 4-F—C$_6$H$_4$ | 4-F—C$_6$H$_4$ | 2HCl | 0.00071 |
| 51 | CH=CH | C(Cl)=CH | 2 | H | 4-F—C$_6$H$_4$ | 4-F—C$_6$H$_4$ | 2HCl | 0.00071 |
| 52 | CH$_2$ | CH$_2$—CH$_2$—CH$_2$ | 2 | H | 4-Cl—C$_6$H$_4$ | 4-Cl—C$_6$H$_4$ | base | 0.00071 |
| 124 | S | CH=C(CH$_3$) | 2 | H | 3-pyridinyl | 4-F—C$_6$H$_4$ | base | 0.0013 |
| 53 | S | CH=CH | 2 | H | 3-pyridinyl | 4-F—C$_6$H$_4$ | base | 0.0013 |
| 54 | CH$_2$ | CH$_2$—CH$_2$—CH$_2$ | 2 | H | 3-pyridinyl | 4-F—C$_6$H$_4$ | base | 0.0028 |
| 55 | CH=C(CH$_3$) | CH=C(CH$_3$) | 2 | H | 4-F—C$_6$H$_4$ | 4-F—C$_6$H$_4$ | 2HCl.H$_2$O | 0.0013 |
| 57 | CH=CH | CH=CH | 2 | H | 3-pyridinyl | 4-F—C$_6$H$_4$ | base | 0.0013 |
| 141 | CH=CH | C(NH$_2$)=CH | 2 | H | 4-F—C$_6$H$_4$ | 4-F—C$_6$H$_4$ | base | 0.00071 |
| 58 | CH=CH | CH=CH | 2 | H | 4-F—C$_6$H$_4$ | 4-F—C$_6$H$_4$ | (E)-2-butene-dioic | 0.00063 |
| 127 | S | C(CH$_3$)=C(CH$_3$) | 2 | H | 4-F—C$_6$H$_4$ | 4-F—C$_6$H$_4$ | 2HCl | 0.00032 |
| 59 | CH=C(CH$_3$) | CH=CH | 2 | H | 4-F—C$_6$H$_4$ | 4-F—C$_6$H$_4$ | 2HCl | 0.00032 |
| 60 | S | CH=CH | 2 | 3-OH | 4-F—C$_6$H$_4$ | 4-F—C$_6$H$_4$ | 2HCl | 0.0013 |
| 61 | CH=CH | CH=CH | 2 | 3-OH | 4-F—C$_6$H$_4$ | 4-F—C$_6$H$_4$ | 2HCl | 0.0022 |
| 62 | CH=CH | CH=CH | 2 | 3-OCH$_3$ | 4-F—C$_6$H$_4$ | 4-F—C$_6$H$_4$ | 2HCl | 0.0028 |
| 63 | S | CH=CH | 2 | 3-OCH$_3$ | 4-F—C$_6$H$_4$ | 4-F—C$_6$H$_4$ | 2HCl | 0.0013 |
| 66 | S | CH=CH | 2 | H | 4-CH$_3$—C$_6$H$_4$ | C$_6$H$_5$ | base | 0.000072 |
| 128 | S | CH$_2$—CH$_2$—CH$_2$ | 2 | H | 4-CH$_3$—C$_6$H$_4$ | C$_6$H$_5$ | 2HCl | 0.00032 |
| 129 | S | CH=C(CH$_3$) | 2 | H | 4-CH$_3$—C$_6$H$_4$ | C$_6$H$_5$ | base | 0.00023 |
| 68 | S | CH=C(CH$_3$) | 2 | H | C$_6$H$_5$ | 3-CH$_3$—C$_6$H$_4$ | base | 0.00032 |
| 69 | S | CH=CH | 2 | H | C$_6$H$_5$ | 3-CH$_3$—C$_6$H$_4$ | (E)-2-butene-dioic acid | 0.00032 |
| 70 | S | CH$_2$—CH$_2$—CH$_2$ | 2 | H | C$_6$H$_5$ | 3-CH$_3$—C$_6$H$_4$ | (E)-2-butene-dioic acid | 0.00056 |
| 71 | CH$_2$ | CH$_2$—CH$_2$—CH$_2$ | 2 | H | 4-CH$_3$—C$_6$H$_4$ | C$_6$H$_5$ | 2HCl | 0.00032 |
| 130 | S | CH$_2$—CH$_2$ | 2 | H | 4-CH$_3$—C$_6$H$_4$ | C$_6$H$_5$ | 2HCl | 0.00008 |
| 72 | S | CH=C(CH$_3$) | 2 | H | C$_6$H$_5$ | 4-OH—C$_6$H$_4$ | base | 0.00071 |
| 73 | S | CH$_2$—CH$_2$ | 2 | H | C$_6$H$_5$ | 4-OH—C$_6$H$_4$ | base | 0.0025 |
| 78 | CH=CH | CH=CH | 2 | H | C$_6$H$_5$ | 4-OH—C$_6$H$_4$ | base | 0.0013 |
| 80 | S | CH=CH | 2 | H | C$_6$H$_5$ | 4-OH—C$_6$H$_4$ | base | 0.0013 |
| 81 | S | CH=C(CH$_3$) | 2 | H | C$_6$H$_5$ | 2-CH$_3$—C$_6$H$_4$ | base | <0.0025 |
| 85 | S | CH=C(CH$_3$) | 2 | H | C$_6$H$_5$ | 3-CF$_3$—C$_6$H$_4$ | base | <0.0025 |
| 86 | CH$_2$ | CH$_2$—CH$_2$—CH$_2$ | 2 | H | C$_6$H$_5$ | 3-CF$_3$—C$_6$H$_4$ | 2HCl | 0.00032 |
| 87 | CH=CH | CH=CH | 2 | H | C$_6$H$_5$ | 3-CF$_3$—C$_6$H$_4$ | 2HCl | <0.0025 |
| 89 | S | CH=CH | 2 | H | C$_6$H$_5$ | 3-CF$_3$—C$_6$H$_4$ | 2HCl | <0.0025 |
| 90 | S | CH$_2$—CH$_2$ | 2 | H | C$_6$H$_5$ | 3-CF$_3$—C$_6$H$_4$ | 2HCl | 0.00071 |
| 92 | CH$_2$ | CH$_2$—CH$_2$—CH$_2$ | 2 | H | C$_6$H$_5$ | 2-CH$_3$—C$_6$H$_4$ | (E)-2-butene-dioic acid | 0.00032 |

Due to their pharmacological activities the compounds of formula (I), their possible stereochemically isomeric forms and their pharmaceutically acceptable acid-addition salts can be used in the treatment of a variety of diseases which are completely or predominantly caused by serotonin. More particularly, the compounds of the present invention may be useful in the treatment of patients suffering from psychosomatic disorders.

The subject compounds have useful properties as sedating-, anxiolytic-, anti-agressive-, anti-stress- and muscular protectant agents and, consequently, they are useful to protect warm-blooded animals, for example, in stress situations.

Moreover, the compounds of the present invention may be used in the treatment of a variety of complaints in which serotonin-release is of non-neglectible importance such as, for example, in the blocking of serotonin-induced contractions of bronchial tissues and of blood vessels, arteries as well as veins.

In view of their useful pharmacological properties the subject compounds may be formulated into various pharmaceutical forms for administration purposes. To prepare the pharmaceutical compositions of this invention, a pharmaceutically effective amount of the particular compound, in base or acid-addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, preferably, for administration orally, rectally or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obiously employed.

For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Acid addition salts of (I), due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier.

Preferred dosage unit forms contain from 1 to 200 mg of active ingredient and particularly preferred dosage unit forms contain from 5 to 100 mg of active ingredient.

Examples of such dosage unit forms are tablets (including scored or coated tablets), capsules, pills, powder packets, wafers, injectable solutions or suspensions, teaspoonfuls, tablespoonfuls and the like, and segregated multiples thereof.

The following formulations exemplify typical pharmaceutical compositions in dosage unit form suitable for systemic administration to animal and human subjects in accordance with the present invention. These examples are given to illustrate and not to limit the scope of the present invention.

ORAL DROPS

The following formulation provides 50 liters of an oral-drop solution comprising 10 mg of 6-[2-[4-[bis(4-fluorophenyl)methylene]-1-piperidinyl]ethyl]-7-methyl-5H-thiazolo[3,2-a]pyrimidin-5-one as the active ingredient (A.I.) per milliliter.

| | |
|---|---|
| A.I. | 500 grams |
| 2-hydroxypropanoic acid | 0.5 liters |
| sodium saccharin | 1750 grams |
| cocoa flavor | 2.5 liters |
| purified water | 2.5 liters |

-continued

| | |
|---|---|
| polyethylene glycol q.s. aq | 50 liters. |

The A.I. was dissolved in the 2-hydroxypropanoic acid and 1.5 liters of the polyethylene glycol at 60°–80° C. After cooling to 30°–40° C. there were added 35 liters of polyethylene glycol and the mixture was stirred well. Then there was added a solution of the sodium saccharin in 2.5 liters of purified water and while stirring there were added the cocoa flavor and polyethylene glycol q.s. ad volume. The resulting solution was filled into suitable containers.

ORAL SOLUTION

The following formulation provides 20 liters of an oral solution comprising 20 mg of 6-[2-[4-[bis(4-fluorophenyl)methylene]-1-piperidinyl]ethyl]-7-methyl-5H-thiazolo[3,2-a]pyrimidin-5-one as the active ingredient (A.I.) per teaspoonful (5 milliliters).

| | |
|---|---|
| A.I. | 20 grams |
| 2,3-dihydroxybutanedioic acid | 10 grams |
| sodium saccharin | 40 grams |
| 1,2,3-propanetriol | 12 liters |
| Sorbitol 70% solution | 3 liters |
| Methyl 4-hydroxybenzoate | 9 grams |
| Propyl 4-hydroxybenzoate | 1 gram |
| Raspberry essence | 2 milliliters |
| Gooseberry essence | 2 milliliters |
| Purified water q.s. ad | 20 liters. |

The methyl and propyl 4-hydroxybenzoates were dissolved in 4 liters of boiling purified water. In 3 liters of this solution were dissolved first the 2,3-dihydroxybutanedioic acid and thereafter the A.I.. The latter solution was combined with the remaining part of the former solution and the 1,2,3-propanetriol and the sorbitol solution were added thereto. The sodium saccharin was dissolved in 0.5 liters of water and the raspberry and gooseberry essences were added. The latter solution was combined with the former, water was added q.s. ad volume and the resulting solution was filled in suitable containers.

CAPSULES

The following formulation provides 1000 capsules comprising each 20 mg of 6-[2-[4-[bis(4-fluorophenyl)methylene]-1-piperidinyl]ethyl]-7-methyl-5H-thiazolo[3,2-a]pyrimidin-5-one as the active ingredient (A.I.).

| | |
|---|---|
| A.I. | 20 grams |
| Sodium lauryl sulfate | 6 grams |
| Starch | 56 grams |
| Lactose | 56 grams |
| Colloidal silicon dioxide | 0.8 grams |
| Magnesium stearate | 1.2 grams |

The composition was prepared by stirring the ingredients vigorously together. The resulting mixture was subsequently filled into suitable hardened gelating capsules.

FILM-COATED TABLETS 10.000 Compressed tablets, each containing as the active ingredient 10 mg of 6-[2-[4-[bis(4-fluorophenyl)methylene]-1-piperidinyl]ethyl]-7-methyl-5H- thiazolo[3,2-a]pyrimidin-5-one, were prepared from the following formulation:

| Tablet core: | |
|---|---|
| A.I. | 100 grams |
| Lactose | 570 grams |
| Starch | 200 grams |
| Polyvinylpyrrolidone (Kollidon-K90) | 10 grams |
| Microcrystalline cellulose (Avicel) | 100 grams |
| Sodium dodecyl sulfate | 5 grams |
| Hydrogenated vegetable oil (Sterotex) | 15 grams |
| Coating: | |
| Methyl cellulose (Methocel 60 HG) | 10 grams |
| Ethyl cellulose (Ethocel 22 cps) | 5 grams |
| 1,2,3-propanetriol | 2.5 milliliters |
| Polyethylene glycol 6000 | 10 grams |
| Concentrated colour suspension (Opaspray K-1-2109) | 30 milliliters |
| Polyvinylpyrrolidone | 5 grams |
| Magnesium octadecanoate | 2.5 grams |

PREPARATION OF TABLET CORE

A mixture of the A.I., the lactose and the starch was mixed well and thereafter humidified with a solution of the sodium dodecyl sulfate and the polyvinylpyrrolidone in about 200 milliliters of water. The wet powder mixture was sieved, dried and sieved again. Then there was added the microcrystalline cellulose and the hydrogenated vegetable oil. The whole was mixed well and compressed into tablets.

Coating

To a solution of the methyl cellulose in 75 milliliters of denaturated ethanol there was added a solution of the ethyl cellulose in 150 milliliters of dichloromethane. Then there were added 75 milliliters of dichloromethane and the 1,2,3-propanetriol. The polyethylene glycol was molten and dissolved in 75 milliliters of dichloromethane. The latter solution was added to the former and then there were added the magnesium octadecanoate, the polyvinylpyrrolidone and the concentrated colour suspension and the whole was homogenated.

The tablet cores were coated with the thus obtained mixture in a coating apparatus.

INJECTABLE SOLUTION

The following formulation provides 1 liter of a parenteral solution comprising 4 mg of 6-[2-[4-[bis(4-fluorophenyl)methylene]-1-piperidinyl]ethyl]-7-methyl-5$\underline{H}$-thiazolo[3,2-a]pyrimidin-5-one as the active ingredient (A.I.) per milliliter.

| A.I. | 4 grams |
|---|---|
| Lactic acid | 4 grams |
| Propylene glycol | 0.05 grams |
| Methyl 4-hydroxybenzoate | 1.8 grams |
| Propyl 4-hydroxybenzoate | 0.2 grams |
| Purified water q.s. ad | 1 liter. |

The methyl and propyl 4-hydroxybenzoates were dissolved in about 0.5 liters of boiling water for injection. After cooling to about 50° C. there were added while stirring the lactic acid, the propylene glycol and the A.I.. The solution was cooled to room temperature and supplemented with water for injection q.s. ad volume. The solution was sterilized by filtration (U.S.P. XVII p. 811) and filled in sterile containers.

SUPPOSITORIES

100 Suppositories each containing 20 mg of 6-[2-[4-[bis(4-fluorophenyl)methylene]-1-piperidinyl]ethyl]-7-methyl-5$\underline{H}$-thiazolo[3,2-a]pyrimidin-5-one as the active ingredient (A.I.) were prepared from the following formulations:

| A.I. | 3 grams |
|---|---|
| 2,3-Dihydroxybutanedioic acid | 3 grams |
| Polyethylene glycol 400 | 25 milliliters |
| Surfactant (Span) | 12 grams |
| Triglycerides (Witepsol 555) q.s. ad | 300 grams. |

The A.I. was dissolved in a solution of the 2,3-dihydroxybutanedioic acid in the polyethylene glycol 400. The surfactant and the triglycerides were molten together. The latter mixture was mixed well with the former solution. The thus obtained mixture was poured onto moulds at a temperature of 37°-38° C. to form the suppositories.

In view of the usefulness of the subject compounds in the treatment of psychosomatic disorders it is evident that the present invention provides a method for treating warm-blooded animals suffering from psychosomatic disorders, said method comprising the systemic administration of a pharmaceutically effective amount of a compound of formula (I), a pharmaceutically acceptable acid addition salt or a stereochemically isomeric form thereof in admixture with a pharmaceutical carrier.

The following examples are intended to illustrate but not to limit the scope of the present invention. Unless otherwise stated all parts herein are by weight and all temperatures are in the centigrade scale.

EXAMPLES

A. Preparation of Intermediates

Example I (a) A mixture of 30 parts of 4-hydroxy-2-mercapto-6-methyl-5-pyrimidineethanol, 25 parts of potassium carbonate, 270 parts of N,N-dimethylacetamide and 75 parts of water was stirred at room temperature and 36 parts of 1,3-dibromopropane were added at once: temperature rose to 50° C. The whole was stirred overnight at room temperature. The reaction mixture was evaporated and water was added to the residue. The solid product was washed with water and dried in vacuo at 100° C., yielding 21 parts (58%) of 3,4-dihydro-7-(2-hydroxyethyl)-8-methyl-2$\underline{H}$,6$\underline{H}$-pyrimido[2,1-b][1,3]thiazin-6-one; mp. 155° C. (intermediate 1).

(b) A mixture of 20 parts of 3,4-dihydro-7-(2-hydroxyethyl)-8-methyl-2$\underline{H}$,6$\underline{H}$-pyrimido[2,1-b][1,3]thiazin-6-one, 50 parts of acetic acid and 180 parts of a hydrobromic acid solution 67% in acetic acid was stirred and heated to reflux. Stirring was continued overnight at reflux temperature. The reaction mixture was evaporated and the solid residue was triturated in 2-propanone. The product was filtered off and dried, yielding 24 parts (100%) of 7-(2-bromoethyl)-3,4-dihydro-8-methyl-2$\underline{H}$,6$\underline{H}$-pyrimido[2,1-b][1,3]thiazin-6-one monohydrobromide; mp. 215° C. (intermediate 2).

Example II (a) To a stirred solution of 40 parts of sodium hydroxide in 500 parts of water were added 400 parts of 2-propanol. In this mixture were dissolved 186.23 parts of 4-hydroxy-2-mercapto-6-methyl-5-pyrimidineethanol. The resulting solution was added dropwise, during a 2.66 hours period, to a stirred and refluxing mixture of 210 parts of sodium hydrogen carbonate, 1635 parts of 1,2-dibromoethane and 1600 parts of 2-propanol. Upon completion, stirring was continued for 2 hours at reflux temperature. The reaction mixture was cooled to room temperature and the solvent was evaporated. The residue was stirred three times in 750 parts of trichloromethane at room temperature. The trichloromethane-phases were evaporated and the residue was crystallized from 300 parts of a mixture of trichloromethane and methanol (85:15 by volume) and 100 parts of hexane. The product was filtered off, washed with 2,2′-oxybispropane and dried in vacuo for 3 hours at 60° C., yielding 51 parts of 2,3-dihydro-6-(2-hydroxyethyl)-7-methyl-5H-thiazolo[3,2-a]pyrimidin-5-one. The mother-liquor was purified by column-chromatography over silica gel using a mixture of trichloromethane and methanol (90:10 by volume) as eluent. The pure fractions were collected and the eluent was evaporated. The residue was boiled in 50 parts of a mixture of trichloromethane and methanol (85:15 by volume). After the addition of 50 parts of hexane, the whole was stirred to room temperature. The product was filtered off, washed with 2,2′-oxybispropane and dried, yielding 17 parts of 2,3-dihydro-6-(2-hydroxyethyl)-7-methyl-5H-thiazolo[3,2-a]pyrimidin-5-one.

Total yield: 68 parts of 2,3-dihydro-6-(2-hydroxyethyl)-7-methyl-5H-thiazolo[3,2-a]pyrimidin-5-one; mp. 148.7° C. (intermediate 3).

(b) To 79.6 parts of 2,3-dihydro-6-(2-hydroxyethyl)-7-methyl-5H-thiazolo[3,2-a]pyrimidin-5-one were added dropwise successively 95 parts of acetic acid and 303 parts of a hydrobromic acid solution 30% in acetic acid at a temperature below 45° C. Upon completion, the whole was heated to reflux and stirring was continued for 17.25 hours at reflux temperature. The reaction mixture was cooled to room temperature. The precipitated product was filtered off and stirred in 152 parts of 2-propanol. The product was filtered off, washed with 40 parts of 2-propanol, dried in vacuo at 50° C. and recrystallized from methanol, yielding 102.3 parts of 6-(2-bromoethyl)-2,3-dihydro-7-methyl-5H-thiazolo[3,2-a]pyrimidin-5-one monohydrobromide; mp. 237.2° C. (intermediate 4).

Example III

A mixture of 50 parts of 2-thiazolamine, 76 parts of 3-acetyl-4,5-dihydro-2(3H)-furanone, 1.2 parts of concentrate hydrochloric acid and 270 parts of methylbenzene was stirred and refluxed for 2 hours using a water-separator. The reaction mixture was cooled and 340 parts of phosphoryl chloride were added at a temperature between 20° and 30° C. The whole was heated slowly to 100°–110° C. and stirring was continued for 2 hours at this temperature. The reaction mixture was evaporated and the residue was poured onto a mixture of crushed ice and ammonium hydroxide. The product was extracted with trichloromethane. The extract was dried, filtered and evaporated. The residue was purified by column-chromatography over silica gel using a mixture of trichloromethane and methanol (95:5 by volume) as eluent. The pure fractions were collected and the eluent was evaporated. The residue was crystallized from a mixture of 2-propanol and 1,1′-oxybisethane, yielding 36 parts of 6-(2-chloroethyl)-7-methyl-5H-thiazolo[3,2-a]pyrimidin-5-one (intermediate 5).

Example IV

A mixture of 30 parts of 4-hydroxy-2-mercapto-6-methyl-5-pyrimidineethanol, 6.8 parts of sodium hydroxide, 15 parts of sodium hydrogen carbonate and 100 parts of 2-propanone was stirred at room temperature and there were added 180 parts of tetrahydrofuran and 170 parts of water. Then there were added at once 25 parts of 3-chloro-2-butanone and 0.2 parts of N,N,N-triethylbenzenemethanaminium chloride and the whole was stirred and heated for 1 hour at 60° C. Stirring was continued overnight at room temperature. The reaction mixture was filtered and the filtrate was salted out. The organic phase was separated, dried, filtered and evaporated, yielding 36 parts of 5-(2-hydroxyethyl)-6-methyl-2-[(1-methyl-2-oxopropyl)thio]-4(3H)-pyrimidinone as an oily residue (intermediate 6).

A mixture of 36 parts of 5-(2-hydroxyethyl)-6-methyl-2-[(1-methyl-2-oxopropyl)thio]-4(3H)-pyrimidinone and 240 parts of a hydrobromic acid solution 60% in acetic acid was stirred and heated for 4 hours at 90° C. The reaction mixture was evaporated and the residue was suspended in 400 parts of 2-propanone. The solid product was filtered off, washed with 2-propanone and dried, yielding 44 parts of 6-(2-bromoethyl)-2,3,7-trimethyl-5H-thiazolo[3,2-a]pyrimidin-5-one monohydrobromide; m.p. 172° C. (intermediate 7).

Example V

A mixture of 90 parts of 5-nitro-2-pyridinamine, 90 parts of 3-acetyl-4,5-dihydro-2(3H)-furanone and 810 parts of methylbenzene was stirred at room temperature. 510 Parts of phosphoryl chloride were added dropwise during a 1 hour-period: the temperature rose to 40° C. The reaction mixture was heated slowly to reflux and the whole was stirred and refluxed for 5 hours. The solvent was evaporated. The hot residue was poured onto a mixture of crushed ice and ammonium hydroxide. After stirring for 30 minutes, the product was extracted with trichloromethane. The extract was dried, filtered and evaporated. The residue was purified by column-chromatography over silica gel using a mixture of trichloromethane and methanol (97:3 by volume) as eluent. The pure fractions were collected and the eluent was evaporated. The residue was crystallized from 2,2′-oxybispropane, yielding 54.8 parts of 3-(2-chloroethyl)-2-methyl-7-nitro-4H-pyrido[1,2-a]pyrimidin-4-one; mp. 170° C. (intermediate 8).

A mixture of 40 parts of 3-(2-chloroethyl)-2-methyl-7-nitro-4H-pyrido[1,2-a]pyrimidin-4-one and 240 parts of methanol was hydrogenated at normal pressure and at room temperature with 0.5 parts of platinum oxide. After the calculated amount of hydrogen was taken up, the catalyst was filtered off and the filtrate was evaporated. The residue was purified by column-chromatography over silica gel using a mixture of trichloromethane and methanol (95:5 by volume) as eluent. The pure fractions were collected and the eluent was evaporated. The residue was converted into the hydrochloride salt in acetonitrile and 2-propanol. The salt was filtered off and dissolved in water while heating. The solution was treated with activated charcoal. The latter was filtered off over Hyflo and the filter-cake was washed with water. The filtrate was stirred in a dilute ammonium hydroxide solution. The precipitated product was filtered off, washed with water and with petroleumether, and dried, yielding 19.4 parts of 7-amino-3-(2-chloroethyl)-2-methyl-4H-pyrido[1,2-a]pyrimidin-4-one; mp. 185° C. (intermediate 9).

Example VI (a) To a stirred and refluxing Grignard complex previously prepared starting from 112.2 parts of 1-bromo-4-methoxybenzene, 15 parts of magnesium and 540 parts of tetrahydrofuran was added dropwise a solution of 84 parts of ethyl 4-(4-fluorobenzoyl)-1-piperidinecarboxylate in 360 parts of tetrahydrofuran. Upon completion, stirring was continued for 2 hours at reflux. After cooling to 10° C., the reaction mixture was poured onto a mixture of 300 parts of crushed ice and 40 parts of acetic acid. The whole was stirred for 5 minutes. 360 Parts of methylbenzene were added. The organic layer was separated, dried, filtered and evaporated, yielding 100 parts of ethyl 4-[(4-fluorophenyl)hydroxy(4-methoxyphenyl)-methyl]-1-piperidinecarboxylate as an oily residue (intermediate 10).

(b) A mixture of 100 parts of ethyl 4-[(4-fluorophenyl)hydroxy(4-methoxyphenyl)methyl]-1-piperidinecarboxylate, 1200 parts of concentrate hydrochloric acid and 160 parts of ethanol was stirred and refluxed for 24 hours. Gaseous hydrogen chloride was introduced till saturation and the whole was further stirred and refluxed for 64 hours. The reaction mixture was evaporated and the oily residue was dissolved in 1000 parts of water while heating. After cooling, the solution was washed twice with 210 parts of 1,1'-oxybisethane and alkalized with ammonium hydroxide. The precipitated product was filtered off and suspended in 160 parts of acetonitrile. The product was filtered off and suspended twice in 80 parts of methanol, yielding, after drying, 44.4 parts (52%) of 4-[(4-fluorophenyl)(4-piperidinylidene)methyl]phenol; mp. 260° C. (intermediate 11).

Example VII (a) To a stirred and refluxing Grignard-complex, previously prepared starting from 70 parts of 1-bromo-4-fluorobenzene and 10 parts of magnesium in 270 parts of tetrahydrofuran, was added dropwise a solution of 25 parts of ethyl 1-(phenylmethyl)-4-piperidinecarboxylate in 90 parts of tetrahydrofuran. Upon completion, stirring was continued for 2 hours at reflux temperature. The reaction mixture was cooled and poured onto a saturate ammonium chloride solution. The organic phase was separated, dried, filtered and evaporated, yielding 40 parts of α,α-bis(4-fluorophenyl)-1-(phenylmethyl)-4-piperidinemethanol as a residue (intermediate 12).

(b) A mixture of 40 parts of α,α-bis(4-fluorophenyl)-1-(phenylmethyl)-4-piperidinemethanol, 120 parts of a hydrochloric acid solution and 50 parts of acetic acid was stirred and refluxed for 2 hours. The reaction mixture was cooled and water and methylbenzene were added: three layers were obtained. The two supernatant phases were separated and treated with ammonium hydroxide. The organic phase was separated, dried, filtered and evaporated. The residue was crystallized from 2,2'-oxybispropane, yielding 26 parts of 4-[bis(4-fluorophenyl)methylene]-1-(phenylmethyl)piperidine (intermediate 13).

(c) A mixture of 1.6 parts of 4-[bis(4-fluorophenyl)-methylene]-1-(phenylmethyl)piperidine and 80 parts of methanol was hydrogenated at normal pressure and at room temperature with 1 part of rhodium-on-charcoal catalyst 5%. After the calculated amount of hydrogen was taken up, the catalyst was filtered off and the filtrate was evaporated, yielding 1.2 parts of 4-[bis(4-fluorophenyl)methylene]piperidine as a residue (intermediate 14).

Example VIII

To a stirred and warm (40° C.) mixture of 600 parts of bromobenzene and 223 parts of aluminum chloride were added portionwise 168.8 parts of 1-acetyl-4-piperidinecarbonyl chloride. Upon completion, stirring was continued for 1 hour at 50° C. and overnight at room temperature. The reaction mixture was poured onto a mixture of 1500 parts of crushed ice and hydrogen chloride. The whole was stirred thoroughly. The precipitated product was filtered off, washed with 2,2'-oxybispropane and dissolved in a mixture of 2250 parts of trichloromethane and 200 parts of water. The layers were separated. The organic layer was dried, filtered and evaporated. The solid residue was suspended in 280 parts of 2,2'-oxybispropane. The product was filtered off and dried, yielding 94 parts (34%) of 1-acetyl-4-(4-bromobenzoyl)piperidine; mp. 120° C. (intermediate 15).

To a stirred and refluxing Grignard-complex previously prepared starting from 52.5 parts of 1-bromo-4-fluorobenzene, 7.5 parts of magnesium and 216 parts of tetrahydrofuran was added dropwise a solution of 94 parts of 1-acetyl-4-(4-bromobenzoyl)piperidine in 450 parts of tetrahydrofuran. Upon completion, stirring was continued for 5 hours at reflux. The reaction mixture was cooled, poured onto a mixture of 300 parts of crushed ice and 40 parts of acetic acid and stirred for 15 minutes. 450 Parts of methylbenzene were added. The organic layer was separated, dried, filtered and evaporated. The residue was taken up in methylbenzene and the whole was evaporated. The residue was purified by column-chromatography over silica gel using a mixture of trichloromethane and methanol (90:10 by volume) as eluent. The pure fractions were collected and the eluent was evaporated, yielding 75 parts of 1-acetyl-α-(4-bromophenyl)-α-(4-fluorophenyl)-4-piperidinemethanol as a residue (intermediate 16).

A mixture of 75 parts of 1-acetyl-α-(4-bromophenyl)-α-(4-fluorophenyl)-4-piperidinemethanol, 600 parts of concentrate hydrochloric acid and 80 parts of ethanol was stirred and refluxed for 18 hours. The reaction mixture was evaporated. 500 Parts of water were added to the residue. The solution was treated with ammonium hydroxide. The product was extracted twice with 375 parts of trichloromethane. The combined organic layers were washed with 100 parts of water, dried, filtered and evaporated. The oily residue was purified by column-chromatography over silica gel using a mixture of trichloromethane and methanol (90:10 by volume), saturated with ammonia, as eluent. The pure fractions were collected and the eluent was evaporated. The residue was converted into the hydrochloride salt in 2-propanol. The whole was evaporated. The residue solidified in 80 parts of acetonitrile. The product was filtered off (filtrate I was set aside) and crystallized from 160 parts of acetonitrile at 0° C. The product was filtered off (filtrate II was set aside) and dried, yielding 36 parts of 4-[(4-bromophenyl)(4-fluorophenyl)methylene]piperidine hydrochloride.

Filtrate I and filtrate II which were set aside (see above), were concentrated to a volume of 40 parts. The concentrate was allowed to crystallize. The product was filtered off and dried, yielding 4 parts of 4-[(4- bromophenyl)(4-fluorophenyl)methylene]piperidine hydrochloride.

Total yield: 40 parts (75%) of 4-[(4-bromophenyl)(4-fluorophenyl)methylene]piperidine hydrochloride (intermediate 17).

Example IX

To a stirred and cooled Grignard-complex previously prepared starting from a mixture of 134 parts of 4-chloro-1-methylpiperidine, 25 parts of magnesium and 652.5 parts of tetrahydrofuran was added dropwise a solution of 170 parts of (4-fluorophenyl)(3-pyridinyl)-methanone in 405 parts of tetrahydrofuran at a temperature between 10°-20° C. Upon completion, stirring was continued for 1 hour at room temperature and for 30 minutes at minutes at reflux. After cooling, the whole was decomposed by pouring onto a mixture of crushed ice and ammonium chloride. 270 Parts of methylbenzene were added. The organic layer was separated, dried, filtered and evaporated. The residue was boiled in acetonitrile with activated charcoal. The latter was filtered off over Hyflo and the filtrate was evaporated, yielding 240 parts (95%) of α-(4-fluorophenyl)-α-(1-methyl-4-piperidinyl)-3-pyridinemethanol as a residue (intermediate 18).

A mixture of 240 parts of α-(4-fluorophenyl)-α-(1-methyl-4-piperidinyl)-3-pyridinemethanol and 900 parts of a hydrobromic acid solution 48% in water was stirred and refluxed for 1 hour. The whole was concentrated to one third of its volume. The concentrate was treated with a sodium hydroxide solution. The product was extracted with 4-methyl-2-pentanone. The extract was dried, filtered and evaporated. The residue was purified by column-chromatography over silica gel using a mixture of trichloromethane and methanol (90:10 by volume), saturated with ammonia, as eluent. The pure fractions were collected and the eluent was evaporated. The residue was crystallized from a mixture of petroleumether and a small amount of 2,2'-oxybispropane (10:1 by volume). The product was filtered off and dried, yielding 112.5 parts (48%) of 3-[(4-fluorophenyl)(1-methyl-4-piperidinylidene)methyl]-pyridine; mp. 93.1° C. (intermediate 19).

To a stirred solution of 180 parts of ethyl carbonochloridate in 600 parts of trichloromethane was added dropwise a solution of 110 parts of 3-[(4-fluorophenyl)(1-methyl-4-piperidinylidene)methyl]pyridine in 600 parts of trichloromethane. Upon completion, the whole was heated till reflux and stirring at reflux was continued for 16 hours. The reaction mixture was evaporated. The residue was stirred in water and the whole was alkalized with a sodium hydroxide solution. The product was extracted with 4-methyl-2-pentanone. The extract was dried, filtered and evaporated, yielding 100 parts (75%) of ethyl 4-[(4-fluorophenyl)(3-pyridinyl)-methylene]-1-piperidinecarboxylate as a residue (intermediate 20).

A mixture of 100 parts of ethyl 4-[(4-fluorophenyl)(3-pyridinyl)methylene]-1-piperidinecarboxylate and 375 parts of a hydrobromic acid solution 48% was stirred and refluxed for 3 hours. The reaction mixture was evaporated. The residue was washed with 2,2'-oxybispropane. The latter was decanted, the residue was stirred in water and the whole was alkalized with a sodium hydroxide solution. The product was extracted with trichloromethane. The extract was dried, filtered and evaporated. The residue was purified by column-chromatography (2x) over silica gel using a mixture of trichloromethane and methanol, saturated with ammonia, (80:20 by volume) as eluent. The main fraction was collected and the eluent was evaporated, yielding 30 parts (37%) of 3-[(4-fluorophenyl)(4-piperidinylidene)-methyl]pyridine as a residue (intermediate 21).

Following the same procedure and starting from the corresponding starting materials there was also prepared:

4-[(4-fluorophenyl)(2-thienyl)methylene]piperidine (intermediate 22).

Example X

To a stirred solution of 50.9 parts of α,α-bis(4-fluorophenyl)-1,2,3,6-tetrahydro-1-(phenylmethyl)-4-pyridinemethanol in 270 parts of tetrahydrofuran were added 750 parts of a hydrochloric acid solution 1N. The whole was stirred first for 7 hours at reflux temperature and then for 8 hours at room temperature. The precipitated product was filtered off and set aside. The filtrate was evaporated till all traces of tetrahydrofuran were removed. After cooling, the solid precipitated product was filtered off and suspended, together with the precipitated product which was set aside (see above), in 80 parts of acetonitrile. The product was filtered off and stirred in 40 parts of acetonitrile while heating. After cooling to 10° C., the product was filtered off and dried, yielding 32.6 parts (58.7%) of 4-[bis(4-fluorophenyl)methylene]-1-(phenylmethyl)-3-piperidinol hydrochloride; mp. 266° C. (intermediate 23).

A mixture of 27.8 parts of 4-[bis(4-fluorophenyl)methylene]-1-(phenylmethyl)-3-piperidinol hydrochloride and 200 parts of methanol was hydrogenated at normal pressure and at room temperature with 3 parts of palladium-on-charcoal catalyst 10%. After the calculated amount of hydrogen was taken up, the catalyst was filtered off and the filtrate was evaporated. The residue was suspended in 80 parts of acetonitrile. The product was filtered off and dried, yielding 21.9 parts (100%) of 4-[bis(4-fluorophenyl)methylene]-3-piperidinol hydrochloride; mp. >260° C. (intermediate 24).

Example XI

To a stirred and cooled (ice-bath) solution of 141.5 parts of 4-pyridinecarbonyl chloride hydrochloride in 400 parts of fluorobenzene were added portionwise 399 parts of aluminum chloride. Upon completion, the whole was slowly heated to reflux and stirring at reflux was continued for 6 hours. The reaction mixture is cooled, poured onto crushed ice and acidified with 240 parts of a hydrochloric acid solution 10N. The layers were separated. The acid aqueous phase was washed twice with 180 parts of methylbenzene and strongly alkalized with a sodium hydroxide solution 60%. The product was extracted three times with dichloromethane. The combined extracts were dried, filtered and evaporated. The residue was dissolved in 900 parts of methylbenzene and the solution was treated with activated charcoal. The latter was filtered off and the filtrate was evaporated. The residue was crystallized from 2,2'-oxybispropane, yielding 152 parts (75.5%) of (4-fluorophenyl)(4-pyridinyl)methanone; mp. 85.5° C. (intermediate 25).

A Grignard-complex was previously prepared starting from 22.75 parts of 1-bromo-4-fluorobenzene, 3.2 parts of magnesium and 45 parts of anhydrous tetrahydrofuran. The whole was cooled in 2-propanone/$CO_2$ to a temperature of −20° to −25° C. A solution of 20.1 parts of (4-fluorophenyl)(4-pyridinyl)methanone in 45 parts of anhydrous methylbenzene was added dropwise, during a 30 minutes-period, at −20° C. Upon completion, the whole was stirred overnight at room temperature. After cooling to 0° C., the reaction mixture was decomposed by the dropwise addition of 50 parts of acetic acid. After stirring for 1 hour at room temperature, the precipitated product was filtered off and set aside. From the filtrate, the organic layer was separated, washed with 50 parts of water, dried, filtered and evaporated. The solid residue and the precipitated product, which was set aside (see above), were washed with water and distilled azeotropically with 180 parts of methylbenzene. The solid distillate was suspended in 80 parts of acetonitrile. The product was filtered off and dried, yielding 28 parts (94%) of α,α-bis(4-fluorophenyl)-4-pyridinemethanol (intermediate 26).

To a stirred mixture of 89.2 parts of α,α-bis(4-fluorophenyl)-4-pyridinemethanol and 720 parts of acetonitrile were added dropwise 56.5 parts of (bromomethyl)benzene at reflux temperature. Upon completion, stirring was continued for 22 hours at reflux. The reaction mixture was allowed to stand over week-end at room temperature. The product was filtered off and set aside. The filtrate was concentrated to a volume of 50 parts. The product was allowed to crystallize. It was filtered off and washed, together with the product which was set aside (see above), with 2,2'-oxybispropane and dried, yielding 139.5 parts (99.2%) of 4-[bis(4-fluorophenyl)-hydroxymethyl]-1-(phenylmethyl)pyridinium bromide (intermediate 27).

To a stirred solution of 140.5 parts of 4-[bis(4-fluorophenyl)hydroxymethyl]-1-(phenylmethyl)pyridinium bromide in 640 parts of methanol were added portionwise, during a 2 hours-period, 15.1 parts of sodium borohydride at room temperature (cooling in ice-water was necessary). Upon completion, the whole was stirred and refluxed for 30 minutes. After cooling to room temperature, 800 parts of water were added. The whole was allowed to stand overnight. The reaction mixture was evaporated till all traces of methanol were removed. 1040 Parts of dichloromethane were added. The layers were separated. The organic layer was washed with 200 parts of water, dried, filtered and evaporated. The residue was taken up in dry methylbenzene and the whole was evaporated, yielding 111 parts (94.5%) of α,α-bis(4-fluorophenyl)-1,2,3,6-tetrahydro-1-(phenylmethyl)-4-pyridinemethanol as an oily residue (intermediate 28).

A mixture of 50.9 parts of α,α-bis(4-fluorophenyl)-1,2,3,6-tetrahydro-1-(phenylmethyl)-4-pyridinemethanol, 320 parts of methanol and 800 parts of a hydrochloric acid solution 1N was stirred first for 3 hours at reflux temperature and then for 56 hours at room temperature. The whole was evaporated till all traces of methanol were removed. The free base was liberated with ammonium hydroxide. The product was extracted with 1040 parts of dichloromethane. The extract was washed with 100 parts of water, dried, filtered and evaporated. The residue was dissolved in 270 parts of N,N-dimethylformamide. The whole was heated to 60° C. 2.5 Parts of a sodium hydride dispersion 50% were added at 80° C. After stirring for 1 hour at 80° C., the mixture was cooled to room temperature. 9 Parts of iodomethane were added dropwise. Upon completion, the whole was stirred and heated for 30 minutes at 40° C. After cooling, the reaction mixture was poured onto 2000 parts of ice-water. The product was extracted twice with 450 parts of methylbenzene. The combined extracts were dried, filtered and evaporated. The oily residue was purifid by column-chromatography over silica gel using a mixture of trichloromethane and methanol (98:2 by volume) as eluent. The pure fractions were collected and the eluent was evaporated, yielding 29.6 parts (57%) of 4-[bis(4-fluorophenyl)methylene]-3-methoxy-1-(phenylmethyl)piperidine as a residue (intermediate 29).

A mixture of 29.6 parts of 4-[bis(4-fluorophenyl)methylene]-3-methoxy-1-(phenylmethyl)piperidine and 200 parts of methanol was hydrogenated at normal pressure and at room temperature with 2 parts of palladium-on-charcoal catalyst 10%. After the calculated amount of hydrogen was taken up, the catalyst was filtered off and the filtrate was evaporated. The residue was purified by column-chromatography over silica gel using first a mixture of trichloromethane and methanol (90:10 by volume) and then a mixture of trichloromethane and methanol (80:20 by volume), saturated with ammonia, as eluent. The pure fractions were collected and the eluent was evaporated. The residue was converted into the hydrochloride salt in 2-propanol. The whole was evaporated. The oily residue was solidified in 70 parts of 1,1'-oxybisethane. The product was filtered off and dried, yielding 16.3 parts (63.4%) of 4-[bis(4-fluorophenyl)methylene]-3-methoxypiperidine hydrochloride (intermediate 30).

Example XII

To a stirred and refluxing Grignard-complex, previously prepared starting from 15 parts of magnesium, 112.2 parts of 1-bromo-4-methoxybenzene and 540 parts of tetrahydrofuran, was added dropwise a solution of 80 parts of ethyl 4-benzoyl-1-piperidinecarboxylate in 360 parts of tetrahydrofuran at reflux temperature. Upon completion, stirring was continued for 2 hours at reflux. After cooling overnight, the reaction mixture was poured onto a mixture of 300 parts of crushed ice and 40 parts of acetic acid at 10° C. After stirring for 15 minutes, the layers were separated. The organic layer was dried, filtered and evaporated. The residue was taken up in methylbenzene and the latter was evaporated. The residue was suspended three times in 70 parts of 2,2'-oxybispropane and the latter was decanted each time. The residue was evaporated to dry, yielding 106 parts of ethyl 4-[hydroxy(4-methoxyphenyl)phenylmethyl]-1-piperidinecarboxylate as a residue (intermediate 31).

A mixture of 106 parts of ethyl 4-[hydroxy(4-methoxyphenyl)phenylmethyl]-1-piperidinecarboxylate, 1200 parts of concentrate hydrochloric acid and 200 parts of ethanol was stirred and refluxed for 18 hours. Gazeous hydrogen chloride was bubbled through the mixture and stirring was continued for 18 hours at reflux temperature. The whole was evaporated. The residue was dissolved in a mixture of 200 parts of ethanol and 1950 parts of a hydrobromic acid solution 48% in water. The mixture was stirred and refluxed overnight. After evaporating, the residue was suspended in 1000 parts of water and treated with ammonium hydroxide. The oil was dissolved in 2100 parts of trichloromethane. The solution was washed with 500 parts of water, dried, filtered and evaporated. The residue was suspended three times in 70 parts of 2,2'-oxybispropane and the latter was evaporated each time. The residue was solidified in 40 parts of acetonitrile. The product was filtered off and dried, yielding 20 parts (25%) of 4-[phenyl(4-piperidinylidene)methyl]phenol; mp.>260° C. (intermediate 32).

Example XIII

To a stirred and refluxing Grignard complex previously prepared starting from 80.2 parts of 4-chloro-1-methylpiperidine, 14.6 parts of magnesium and 270 parts of tetrahydrofuran, was added dropwise a solution of 101 parts of (2-fluorophenyl)phenylmethanone in 450 parts of tetrahydrofuran. Upon completion, stirring was continued for 18 hours at reflux temperature. The reaction mixture was cooled in an ice-bath and decomposed with a solution of 32 parts of ammonium chloride in 160 parts of water. After stirring for 30 minutes, the product was filtered off and washed with tetrahydrofuran. The filtrate was evaporated, the residue was taken up in methylbenzene and the latter was evaporated again in a boiling water-bath. The residue was dissolved in 700 parts of 2,2'-oxybispropane. The turbid solution was filtered and gaseous hydrogen chloride was bubbled through the filtrate. The solid product was filtered off and suspended in 1000 parts of water. The suspension was treated with ammonium hydroxide and extracted twice with 280 parts of 1,1'-oxybisethane. The combined extracts were dried, filtered and evaporated. The oily residue was crystallized from 240 parts of acetonitrile. After cooling to 0° C., the product was filtered off and dried, yielding 66 parts (44%) of α-(2-fluorophenyl)-1-methyl-α-phenyl-4-piperidinemethanol (intermediate 33).

To a stirred mixture of 66.0 parts of α-(2-fluorophenyl)-1-methyl-α-phenyl-4-piperidinemethanol and 450 parts of methylbenzene were added dropwise 28.2 parts of ethyl carbonochloridate. Upon completion, stirring was continued overnight at reflux temperature. The reaction mixture was diluted with 630 parts of dimethylbenzene and the whole was stirred and refluxed overnight. The precipitate was filtered off and the filtrate was evaporated. The residue solidified on stirring in 210 parts of 2,2'-oxybispropane. The product was filtered off and dried, yielding 27 parts (34.5%) of ethyl 4-[(2-fluorophenyl)hydroxyphenylmethyl]-1-piperidinecarboxylate (intermediate 34).

A mixture of 26.0 parts of ethyl 4-[(2-fluorophenyl)hydroxyphenylmethyl]-1-piperidinecarboxylate and 375 parts of a hydrobromic acid solution 48% in water was stirred and refluxed for 60 hours. The reaction mixture was evaporated and the residue was suspended in 250 parts of water. The whole was treated with ammonium hydroxide and stirred for 1 hour at room temperature. The product was extracted three times with 300 parts of trichloromethane. The combined extracts were dried, filtered and evaporated. The residue was purified by column-chromatography over silica gel using a mixture of trichloromethane and methanol saturated with ammonia (90:10 by volume) as eluent. The pure fractions were collected and the eluent was evaporated. The residue was converted into the hydrochloride salt in 2-propanol. The whole was evaporated and the solid residue was suspended in 80 parts of acetonitrile. The product was filtered off and dried, yielding 14.3 parts (65%) of 4-[(2-fluorophenyl)phenylmethylene]piperidine hydrochloride; mp. +260° C. (intermediate 35).

B. Preparation of Final Compounds

Example XIV

A mixture of 3.8 parts of 6-(2-chloroethyl)-7-methyl-5H-thiazolo[3,2-a]pyrimidin-5-one, 3.5 parts of 4-[bis(4-fluorophenyl)methylene]piperidine, 10 parts of sodium carbonate, 0.1 parts of potassium iodide and 240 parts of 4-methyl-2-pentanone was stirred and refluxed for 20 hours using a water-separator. The reaction mixture was filtered hot and the filtrate was evaporaed. The residue was purified by column-chromatography over silica gel using a mixture of trichloromethane and methanol (95:5 by volume) as eluent. The pure fractions were collected and the eluent was evaporated. The residue was crystallized from acetonitrile, yielding 2.8 parts of 6-[2-[4-[bis(4-fluorophenyl)methylene]-1-piperidinyl]ethyl]-7-methyl-5H-thiazolo[3,2-a]pyrimidin-5-one; mp. 145.5° C. (compound 1).

Following the same procedure and using equivalent amounts of the appropriate starting materials there were also prepared:

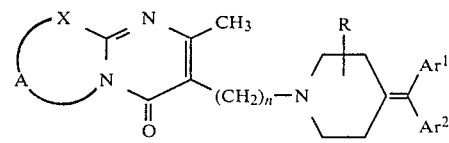

| No. | X | A | n | R | Ar¹ | Ar² | base/salt form | mp. °C. |
|---|---|---|---|---|---|---|---|---|
| 2 | CH=CH | CH=CH | 2 | H | 4-F—C$_6$H$_4$ | 4-F—C$_6$H$_4$ | 2HCl | 205.8 |
| 3 | CH$_2$ | CH$_2$—CH$_2$—CH$_2$ | 2 | H | 4-F—C$_6$H$_4$ | 4-F—C$_6$H$_4$ | base | 169.3 |
| 4 | S | CH=CH | 2 | H | C$_6$H$_5$ | C$_6$H$_5$ | base | 148.3 |
| 5 | S | CH$_2$—CH$_2$ | 2 | H | 4-F—C$_6$H$_4$ | 3-Cl—C$_6$H$_4$ | base | 146.2 |
| 6 | S | CH=CH | 2 | H | 4-F—C$_6$H$_4$ | 3-Cl—C$_6$H$_4$ | base | 147.0 |
| 7 | S | CH=C(CH$_3$) | 2 | H | 4-F—C$_6$H$_4$ | 3-Cl—C$_6$H$_4$ | base | 149.6 |
| 8 | S | CH$_2$—CH$_2$—CH$_2$ | 2 | H | 4-F—C$_6$H$_4$ | 3-Cl—C$_6$H$_4$ | HCl | 276.1 |
| 9 | S | CH=CH | 2 | H | 4-F—C$_6$H$_4$ | 4-Cl—C$_6$H$_4$ | base | 155.2 |
| 10 | S | CH=C(CH$_3$) | 2 | H | 4-F—C$_6$H$_4$ | 4-Cl—C$_6$H$_4$ | base | 158.3 |
| 11 | CH$_2$ | CH$_2$—CH$_2$—CH$_2$ | 2 | H | 4-F—C$_6$H$_4$ | 4-Cl—C$_6$H$_4$ | base | 138.5 |
| 12 | S | CH$_2$—CH$_2$—CH$_2$ | 2 | H | 4-F—C$_6$H$_4$ | 4-Cl—C$_6$H$_4$ | base | 151.3 |
| 13 | CH=CH | CH=CH | 2 | H | 4-F—C$_6$H$_4$ | 4-Cl—C$_6$H$_4$ | base | 121.4 |
| 14 | S | CH=CH | 2 | H | 4-F—C$_6$H$_4$ | 3-CH$_3$—C$_6$H$_4$ | base | 131.2 |
| 15 | CH=CH | CH=CH | 2 | H | 4-F—C$_6$H$_4$ | 3-CH$_3$—C$_6$H$_4$ | base | 133.7 |
| 16 | CH=CH | CH=CH | 2 | H | 4-F—C$_6$H$_4$ | 3-Cl—C$_6$H$_4$ | (E)-2-butenedioic acid | 239.9 |
| 17 | CH$_2$ | CH$_2$—CH$_2$—CH$_2$ | 2 | H | 4-F—C$_6$H$_4$ | 3-Cl—C$_6$H$_4$ | (E)-2-butenedioic acid | 232.4 |
| 18 | CH=CH | CH=CH | 2 | H | C$_6$H$_5$ | C$_6$H$_5$ | base | 141.6 |

-continued

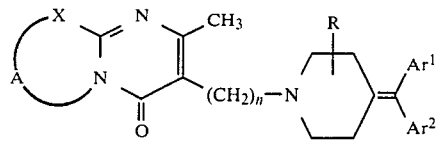

| No. | X | A | n | R | Ar¹ | Ar² | base/salt form | mp. °C. |
|---|---|---|---|---|---|---|---|---|
| 19 | $CH_2$ | $CH_2-CH_2-CH_2$ | 2 | H | $C_6H_5$ | $C_6H_5$ | base | 159.7 |
| 20 | CH=CH | CH=CH | 2 | H | 4-F—$C_6H_4$ | 4-OH—$C_6H_4$ | base | 200.3 |
| 21 | S | CH=CH | 2 | H | 4-F—$C_6H_4$ | 3-$CF_3$—$C_6H_4$ | 2HCl | 214.4 |
| 22 | S | $CH_2-CH_2$ | 2 | H | 4-F—$C_6H_4$ | 4-Cl—$C_6H_4$ | HCl.$H_2O$ | 248.0 |
| 23 | S | CH=C($CH_3$) | 2 | H | 4-F—$C_6H_4$ | 4-OH—$C_6H_4$ | base | 230.7 |
| 24 | S | CH=CH | 2 | H | 4-F—$C_6H_4$ | 4-OH—$C_6H_4$ | base | 188.7 |
| 25 | S | CH=CH | 2 | H | 4-F—$C_6H_4$ | 3-F—$C_6H_4$ | (E)-2-butene-dioic acid | 255.8 |
| 26 | S | CH=CH | 2 | H | 4-$CH_3$—$C_6H_4$ | 4-$CH_3$—$C_6H_4$ | base | 127.1 |
| 27 | S | CH=C($CH_3$) | 2 | H | 4-F—$C_6H_4$ | 3-F—$C_6H_4$ | (E)-2-butene-dioic acid | 255.1 |
| 28 | S | $CH_2-CH_2$ | 2 | H | 4-F—$C_6H_4$ | 3-F—$C_6H_4$ | (E)-2-butene-dioic acid | 229.8 |
| 29 | S | $CH_2-CH_2-CH_2$ | 2 | H | 4-F—$C_6H_4$ | 4-F—$C_6H_4$ | (E)-2-butene-dioic acid | 230.9 |
| 30 | $CH_2$ | $CH_2-CH_2-CH_2$ | 2 | H | 4-F—$C_6H_4$ | 3-F—$C_6H_4$ | (E)-2-butene-dioic acid | 230.0 |
| 31 | CH=CH | CH=CH | 2 | H | 4-F—$C_6H_4$ | 3-$CF_3$—$C_6H_4$ | 2HCl | 239.9 |
| 32 | S | CH=C($CH_3$) | 2 | H | 4-F—$C_6H_4$ | 4-Br—$C_6H_4$ | base | 147.8 |
| 33 | S | $CH_2-CH_2-CH_2$ | 2 | H | 4-F—$C_6H_4$ | 4-Br—$C_6H_4$ | base | 99.0 |
| 34 | S | CH=CH | 2 | H | 4-F—$C_6H_4$ | 4-Br—$C_6H_4$ | base | 158.7 |
| 35 | $CH_2$ | $CH_2-CH_2-CH_2$ | 2 | H | 4-F—$C_6H_4$ | 4-Br—$C_6H_4$ | base | 72.3 |
| 36 | CH=CH | CH=CH | 2 | H | 4-F—$C_6H_4$ | 3-F—$C_6H_4$ | (E)-2-butene-dioic acid | 244.2 |
| 37 | S | $CH_2-CH_2-CH_2$ | 2 | H | 4-F—$C_6H_4$ | 4-OH—$C_6H_4$ | base | 206.3 |
| 38 | S | CH=C($CH_3$) | 2 | H | 4-F—$C_6H_4$ | 4-$CH_3$—$C_6H_4$ | base | 128.0 |
| 39 | $CH_2$ | $CH_2-CH_2-CH_2$ | 2 | H | 4-F—$C_6H_4$ | 4-OH—$C_6H_4$ | base | 225.2 |
| 40 | S | $CH_2-CH_2-CH_2$ | 2 | H | 4-F—$C_6H_4$ | 4-$CH_3$—$C_6H_4$ | (E)-2-butene-dioic | 256.1 |
| 41 | CH=CH | CH=CH | 2 | H | 4-F—$C_6H_4$ | 4-$CH_3$—$C_6H_4$ | (E)-2-butene-dioic | 253.6 |
| 42 | $CH_2$ | $CH_2-CH_2-CH_2$ | 2 | H | 4-F—$C_6H_4$ | 4-$CH_3$—$C_6H_4$ | 2HCl | 246.2 |
| 43 | CH=CH | CH=CH | 2 | H | 4-$CH_3$—$C_6H_4$ | 4-$CH_3$—$C_6H_4$ | 2HCl | >300 |
| 44 | S | $CH_2-CH_2$ | 2 | H | 4-F—$C_6H_4$ | 4-Br—$C_6H_4$ | HCl | 232.0 |
| 45 | CH=CH | CH=CH | 2 | H | 4-F—$C_6H_4$ | 4-Br—$C_6H_4$ | base | 115.1 |
| 46 | $CH_2$ | $CH_2-CH_2-CH_2$ | 2 | H | 4-F—$C_6H_4$ | 4-$CH_3$—$C_6H_4$ | (E)-2-butene-dioic | 223.5 |
| 47 | S | $CH_2-CH_2$ | 2 | | 4-F—$C_6H_4$ | 4-$CH_3$—$C_6H_4$ | (E)-2-butene-dioic | 245.7 |
| 48 | S | CH=CH | 2 | H | 4-Cl—$C_6H_4$ | 4-Cl—$C_6H_4$ | base | 131.7 |
| 49 | S | CH=CH | 2 | H | 4-F—$C_6H_4$ | 4-$CH_3$—$C_6H_4$ | (E)-2-butene-dioic | 255.3 |
| 50 | CH=CH | C($CH_3$)=CH | 2 | H | 4-F—$C_6H_4$ | 4-F—$C_6H_4$ | 2HCl | 264.8 |
| 51 | CH=CH | C(Cl)=CH | 2 | H | 4-F—$C_6H_4$ | 4-F—$C_6H_4$ | 2HCl | 280.1 |
| 52 | $CH_2$ | $CH_2-CH_2-CH_2$ | 2 | H | 4-Cl—$C_6H_4$ | 4-Cl—$C_6H_4$ | base | 168.1 |
| 53 | S | CH=CH | 2 | H | 3-pyridinyl | 4-F—$C_6H_4$ | base | 131.8 |
| 54 | $CH_2$ | $CH_2-CH_2-CH_2$ | 2 | H | 3-pyridinyl | 4-F—$C_6H_4$ | base | 138.7 |
| 55 | CH=C($CH_3$) | CH=C($CH_3$) | 2 | H | 4-F—$C_6H_4$ | 4-F—$C_6H_4$ | 2HCl.$H_2O$ | 210.2 |
| 56 | CH=CH | C(Br)=CH | 2 | H | 4-F—$C_6H_4$ | 4-F—$C_6H_4$ | 2HCl.$H_2O$ | 208.0 |
| 57 | CH=CH | CH=CH | 2 | H | 3-pyridinyl | 4-F—$C_6H_4$ | base | 100.5 |
| 58 | CH=CH | CH=CH | 2 | H | 4-F—$C_6H_4$ | 4-F—$C_6H_4$ | (E)-2-butene-dioic | 248.0 |
| 59 | CH=C($CH_3$) | CH=CH | 2 | H | 4-F—$C_6H_4$ | 4-F—$C_6H_4$ | 2HCl | 238.3 |
| 60 | S | CH=CH | 2 | 3-OH | 4-F—$C_6H_4$ | 4-F—$C_6H_4$ | 2HCl | 196.6 |
| 61 | CH=CH | CH=CH | 2 | 3-OH | 4-F—$C_6H_4$ | 4-F—$C_6H_4$ | 2HCl | 214.9 |
| 62 | CH=CH | CH=CH | 2 | 3-$OCH_3$ | 4-F—$C_6H_4$ | 4-F—$C_6H_4$ | 2HCl | 210.7 |
| 63 | S | CH=CH | 2 | 3-$OCH_3$ | 4-F—$C_6H_4$ | 4-F—$C_6H_4$ | 2HCl | 198.1 |
| 64 | CH=CH | CH=CH | 4 | H | 4-F—$C_6H_4$ | 4-F—$C_6H_4$ | 2HCl | 228.9 |
| 65 | CH=CH | CH=CH | 3 | H | 4-F—$C_6H_4$ | 4-F—$C_6H_4$ | 2HCl | 187.4 |
| 66 | S | CH=CH | 2 | H | 4-$CH_3$—$C_6H_4$ | $C_6H_5$ | base | 157.7 |
| 67 | CH=CH | CH=CH | 2 | H | 4-$CH_3$—$C_6H_4$ | $C_6H_5$ | base | 142.0 |
| 68 | S | CH=C($CH_3$) | 2 | H | $C_6H_5$ | 3-$CH_3$—$C_6H_4$ | base | 154.6 |
| 69 | S | CH=CH | 2 | H | $C_6H_5$ | 3-$CH_3$—$C_6H_4$ | (E)-2-butene-dioic acid | 267.5 |
| 70 | S | $CH_2-CH_2-CH_2$ | 2 | H | $C_6H_5$ | 3-$CH_3$—$C_6H_4$ | (E)-2-butene-dioic acid | 244.9 |
| 71 | $CH_2$ | $CH_2-CH_2-CH_2$ | 2 | H | 4-$CH_3$—$C_6H_4$ | $C_6H_5$ | 2HCl | 263.5 |
| 72 | S | CH=C($CH_3$) | 2 | H | $C_6H_5$ | 4-OH—$C_6H_4$ | base | 237.1 |
| 73 | S | $CH_2-CH_2$ | 2 | H | $C_6H_5$ | 4-OH—$C_6H_4$ | base | 213.4 |
| 74 | $CH_2$ | $CH_2-CH_2-CH_2$ | 2 | H | $C_6H_5$ | 4-OH—$C_6H_4$ | base | 202.5 |
| 75 | $CH_2$ | $CH_2-CH_2-CH_2$ | 2 | H | $C_6H_5$ | 3-$CH_3$—$C_6H_4$ | (E)-2-butene-dioic acid | 238.1 |

-continued

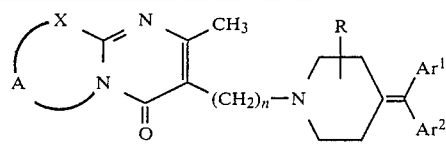

| No. | X | A | n | R | Ar¹ | Ar² | base/salt form | mp. °C. |
|---|---|---|---|---|---|---|---|---|
| 76 | S | CH₂—CH₂—CH₂ | 2 | H | C₆H₅ | 2-CH₃—C₆H₄ | (E)-2-butenedioic acid | 252.0 |
| 77 | CH=CH | CH=CH | 2 | H | C₆H₅ | 3-CH₃—C₆H₄ | (E)-2-butenedioic acid | 271.3 |
| 78 | CH=CH | CH=CH | 2 | H | C₆H₅ | 4-OH—C₆H₄ | base | 215.5 |
| 79 | S | CH₂—CH₂—CH₂ | 2 | H | C₆H₅ | 4-OH—C₆H₄ | base | 210.0 |
| 80 | S | CH=CH | 2 | H | C₆H₅ | 4-OH—C₆H₄ | base | 201.4 |
| 81 | S | CH=C(CH₃) | 2 | H | C₆H₅ | 2-CH₃—C₆H₄ | base | 161.6 |
| 82 | S | CH₂—CH₂ | 2 | H | C₆H₅ | 3-CH₃—C₆H₄ | (E)-2-butenedioic acid | 251.1 |
| 83 | CH=CH | CH=CH | 2 | H | C₆H₅ | 2-CH₃—C₆H₄ | (E)-2-butenedioic acid | 245.7 |
| 84 | S | CH₂—CH₂ | 2 | H | C₆H₅ | 2-CH₃—C₆H₄ | (E)-2-butenedioic acid | 236.1 |
| 85 | S | CH=C(CH₃) | 2 | H | C₆H₅ | 3-CF₃—C₆H₄ | base | 140.7 |
| 86 | CH₂ | CH₂—CH₂—CH₂ | 2 | H | C₆H₅ | 3-CF₃—C₆H₄ | 2HCl | 272.0 |
| 87 | CH=CH | CH=CH | 2 | H | C₆H₅ | 3-CF₃—C₆H₄ | 2HCl | 261.4 |
| 88 | S | CH₂—CH₂—CH₂ | 2 | H | C₆H₅ | 3-CF₃—C₆H₄ | 2HCl | 278.3 |
| 89 | S | CH=CH | 2 | H | C₆H₅ | 3-CF₃—C₆H₄ | 2HCl | 213.5 |
| 90 | S | CH₂—CH₂ | 2 | H | C₆H₅ | 3-CF₃—C₆H₄ | 2HCl | 257.7 |
| 91 | S | CH=CH | 2 | H | C₆H₅ | 2-CH₃—C₆H₄ | (E)-2-butenedioic acid | 253.3 |
| 92 | CH₂ | CH₂—CH₂—CH₂ | 2 | H | C₆H₅ | 2-CH₃—C₆H₄ | (E)-2-butenedioic acid | 229.8 |
| 93 | CH=CH | CH=CH | 2 | H | 3-Cl—C₆H₄ | C₆H₅ | (E)-2-butenedioic acid | 255.5 |
| 94 | S | CH=CH | 2 | H | C₆H₅ | 3-pyridinyl | (E)-2-butenedioic acid | 241.0 |
| 95 | CH=CH | CH=CH | 2 | H | 2-F—C₆H₄ | C₆H₅ | 2HCl | 260.7 |
| 96 | CH₂ | CH₂—CH₂—CH₂ | 2 | H | C₆H₅ | 3-pyridinyl | (E)-2-butenedioic acid | 211.2 |
| 97 | CH=CH | CH=CH | 2 | H | C₆H₅ | 3-pyridinyl | (E)-2-butenedioic acid | 240.2 |
| 98 | S | CH=CH | 2 | H | 3-Cl—C₆H₄ | C₆H₅ | (E)-2-butenedioic acid | 259.1 |
| 99 | CH₂ | CH₂—CH₂—CH₂ | 2 | H | 3-Cl—C₆H₄ | C₆H₅ | (E)-2-butenedioic acid | 252.0 |
| 100 | S | CH₂—CH₂—CH₂ | 2 | H | 2-F—C₆H₄ | C₆H₅ | base | 150.2 |
| 101 | S | CH=CH | 2 | H | 2-F—C₆H₄ | C₆H₅ | base | 134.6 |
| 102 | CH₂ | CH₂—CH₂—CH₂ | 2 | H | 2-F—C₆H₄ | C₆H₅ | 2HCl | 265.4 |
| 103 | CH=CH | CH=CH | 2 | H | 2-thienyl | 4-F—C₆H₄ | base | |

Example XV

A mixture of 7.4 parts of 7-(2-bromoethyl)-3,4-dihydro-8-methyl-2H,6H-pyrimido[2,1-b][1,3]thiazin-6-one monohydrobromide, 6.6 parts of 4-(diphenylmethylene)piperidine hydrobromide, 12 parts of sodium carbonate and 120 parts of 4-methyl-2-pentanone was stirred and refluxed overnight. The reaction mixture was cooled, water was added and the layers were separated. The organic phase was dried, filtered and evaporated. The residue was purified by column-chromatography over silica gel using a mixture of trichloromethane and methanol (95:5 by volume) as eluent. The pure fractions were collected and the eluent was evaporated. The residue was crystallized from a mixture of 4-methyl-2-pentanone and 2,2'-oxybispropane. The product was filtered off and recrystallized from 2-propanol, yielding 5.5 parts (60%) of 7-[2-[4-(diphenylmethylene)-1-piperidinyl]ethyl]-3,4-dihydro-8-methyl-2H,6H-pyrimido[2,1-b][1,3]-thiazin-6-one; mp. 176.0° C. (compound 104).

Following the same procedure and using equivalent amounts of the appropriate starting materials there were also prepared:

6-[2-[4-(diphenylmethylene)-1-piperidinyl]ethyl]-3,7-dimethyl-5H-thiazolo[3,2-a]pyrimidin-5-one; mp. 150.6° C. (compound 105);

6-[2-[4-[bis(4-methylphenyl)methylene]-1-piperidinyl]ethyl]-3,7-dimethyl-5H-thiazolo[3,2-a]pyrimidin-5-one; mp. 167.8° C. (compound 106);

6-[2-[4-(diphenylmethylene)-1-piperidinyl]ethyl]-2,3-dihydro-7-methyl-5H-thiazolo[3,2-a]pyrimidin-5-one dihydrochloride; mp. 271.1° C. (compound 107);

7-[2-[4-[bis(4-methylphenyl)methylene]-1-piperidinyl]ethyl]-3,4-dihydro-8-methyl-2H,6H-pyrimido[2,1-b][1,3]thiazin-6-one; mp. 124.0° C. (compound 108);

6-[2-[4-[bis(4-methylphenyl)methylene]-1-piperidinyl]ethyl]-2,3-dihydro-7-methyl-5H-thiazolo[3,2-a]pyrimidin-5-one dihydrochloride.monohydrate; mp. 117.1° C. (compound 109);

6-[2-[4-[bis(4-chlorophenyl)methylene]-1-piperidinyl]ethyl]-2,3-dihydro-7-methyl-5H-thiazolo[3,2-a]pyrimidin-5-one; mp. 177.5° C. (compound 110); and 6-[2-[4-[(4-fluorophenyl)phenylmethylene]-1-piperidinyl]ethyl]-7-methyl-5H-thiazolo[3,2-a]pyrimidin-5-one; mp. 126.2° C. (compound 111).

Example XVI

A mixture of 5.6 parts of 6-(2-bromoethyl)-3,7-dimethyl-5H-thiazolo[3,2-a]pyrimidin-5-one monohydrobromide, 3.5 parts of 4-[bis(4-fluorophenyl)methylene]piperidine, 1 part of a sodium methoxide solution 30%, 8 parts of sodium carbonate and 240 parts of 4-methyl-2-pentanone was stirred and refluxed for 20 hours using a water-separator. The reaction mixture was filtered while hot and the filtrate was evaporated. The residue was purified by column-chromatography over silica gel using a mixture of trichloromethane and methanol (95:5 by volume) as eluent. The pure fractions were collected and the eluent was evaporated. The residue was crystallized from acetonitrile, yielding 4.3 parts (72.8%) of 6-[2-[4-[bis(4-fluorophenyl)methylene]-1-piperidinyl]ethyl]-3,7-dimethyl-5H-thiazolo[3,2-a]pyrimidin-5-one; mp. 183.8° C. (compound 112).

filtrate was evaporated. The residue was purified by column-chromatography over silica gel using a mixture of trichloromethane and methanol (92:8 by volume) as eluent. The pure fractions were collected and the eluent was evaporated. The residue was converted into the hydrochloride salt in acetonitrile and 2-propanol. The salt was filtered off and dried, yielding 4.8 parts (60%) of 3-[2-[4-[(4-fluorophenyl)phenylmethylene]-1-piperidinyl]ethyl]-6,7,8,9-tetrahydro-2-methyl-4H-pyrido[1,2-a]pyrimidin-4-one dihydrochloride; mp. 264.6° C. (compound 137).

Following the same procedure and using equivalent amounts of the appropriate starting materials there were also prepared:

3-[2-[4-[(4-fluorophenyl)(3-methylphenyl)methylene]-1-piperidinyl]ethyl]-6,7,8,9-tetrahydro-2-methyl-4H-pyrido[1,2-a]pyrimidin-4-one; mp. 166.0° C. (compound 138);

6-[2-[4-[(4-fluorophenyl)phenylmethylene]-1-piperidinyl]ethyl]-7-methyl-5H-thiazolo[3,2-a]pyrimidin-5-one monohydrochloride; mp. 239.3° C.

Following the same procedure and using equivalent amounts of
the appropriate starting materials there were also prepared:

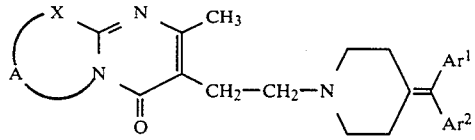

| No. | X | A | Ar$^1$ | Ar$^2$ | base/salt form | mp. °C. |
|---|---|---|---|---|---|---|
| 113 | S | CH$_2$—CH$_2$ | 4-F—C$_6$H$_4$ | 4-F—C$_6$H$_4$ | 2HCl | 248.3 |
| 114 | S | CH$_2$—CH$_2$—CH$_2$ | 4-F—C$_6$H$_4$ | 4-F—C$_6$H$_4$ | base | 173.2 |
| 115 | S | CH$_2$—CH$_2$—CH$_2$ | 4-F—C$_6$H$_4$ | C$_6$H$_5$ | 2HCl | 273.3 |
| 116 | S | CH$_2$—CH$_2$ | 4-F—C$_6$H$_4$ | C$_6$H$_5$ | 2HCl.H$_2$O | 251.5 |
| 117 | S | CH=C(CH$_3$) | 4-F—C$_6$H$_4$ | C$_6$H$_5$ | HCl | 184.7 |
| 118 | S | CH$_2$—CH$_2$ | 4-F—C$_6$H$_4$ | 3-CF$_3$—C$_6$H$_4$ | 2HCl | 231.2 |
| 119 | S | CH=C(CH$_3$) | 4-F—C$_6$H$_4$ | 3-CF$_3$—C$_6$H$_4$ | base | 134.8 |
| 120 | S | CH$_2$—CH$_2$—CH$_2$ | 4-F—C$_6$H$_4$ | 3-CF$_3$—C$_6$H$_4$ | 2HCl | 272.3 |
| 121 | S | CH$_2$—CH$_2$—CH$_2$ | 4-F—C$_6$H$_4$ | 3-CH$_3$—C$_6$H$_4$ | base | 151.5 |
| 122 | S | CH=C(CH$_3$) | 4-F—C$_6$H$_4$ | 3-CH$_3$—C$_6$H$_4$ | base | 136.1 |
| 123 | S | CH$_2$—CH$_2$—CH$_2$ | 4-F—C$_6$H$_4$ | 3-CH$_3$—C$_6$H$_4$ | 2HCl | 259.5 |
| 124 | S | CH=C(CH$_3$) | 3-pyridinyl | 4-F—C$_6$H$_4$ | base | 159.3 |
| 125 | S | CH$_2$—CH$_2$ | 3-pyridinyl | 4-F—C$_6$H$_4$ | base | 122.5 |
| 126 | S | CH$_2$—CH$_2$—CH$_2$ | 3-pyridinyl | 4-F—C$_6$H$_4$ | base | 125.3 |
| 127 | S | C(CH$_3$)=C(CH$_3$) | 4-F—C$_6$H$_4$ | 4-F—C$_6$H$_4$ | 2HCl | 150.7 |
| 128 | S | CH$_2$—CH$_2$—CH$_2$ | 4-CH$_3$—C$_6$H$_4$ | C$_6$H$_5$ | 2HCl | 277.7 |
| 129 | S | CH=C(CH$_3$) | 4-CH$_3$—C$_6$H$_4$ | C$_6$H$_5$ | base | 128.7 |
| 130 | S | CH$_2$—CH$_2$ | 4-CH$_3$—C$_6$H$_4$ | C$_6$H$_5$ | 2HCl | 247.3 |
| 131 | S | CH$_2$—CH$_2$—CH$_2$ | 3-Cl—C$_6$H$_4$ | C$_6$H$_5$ | (E)-2-butenedioic acid | 241.1 |
| 132 | S | CH=C(CH$_3$) | 3-Cl—C$_6$H$_4$ | C$_6$H$_5$ | (E)-2-butenedioic acid | 249.9 |
| 133 | S | CH=C(CH$_3$) | C$_6$H$_5$ | 3-pyridinyl | (E)-2-butenedioic acid | 226.0 |
| 134 | S | CH$_2$—CH$_2$—CH$_2$ | C$_6$H$_5$ | 3-pyridinyl | (E)-2-butenedioic acid | 227.3 |
| 135 | S | CH$_2$—CH$_2$ | 3-Cl—C$_6$H$_4$ | C$_6$H$_5$ | (E)-2-butenedioic acid | 252.5 |
| 136 | S | CH$_2$—CH$_2$ | C$_6$H$_5$ | 3-pyridinyl | (E)-2-butenedioic acid | 211.3 |

Example XVII

A mixture of 4.5 parts of 3-(2-chloroethyl)-6,7,8,9-tetrahydro-2-methyl-4H-pyrido[1,2-a]pyrimidin-4-one monohydrochloride, 4.6 parts of 4-[(4-fluorophenyl)phenylmethylene]piperidine hydrochloride, 2 parts of a sodium methoxide solution 30%, 8 parts of sodium carbonate, 0.2 parts of potassium iodide and 240 parts of 4-methyl-2-pentanone was stirred and refluxed for 22 hours. The reaction mixture was filtered hot and the (compound 139);

3-[2-[4-[(4-fluorophenyl)[3-(trifluoromethyl)phenyl]methylene]-1-piperidinyl]ethyl]-6,7,8,9-tetrahydro-2-methyl-4H-pyrido[1,2-a]pyrimidin-4-one dihydrochloride; mp. 254.0° C. (compound 140); and 7-amino-3-[2-[4-[bis(4-fluorophenyl)methylene]-1-piperidinyl]ethyl]-2-methyl-4H-pyrido[1,2-a]-pyrimidin-4-one; mp. 209.9° C. (compound 141)

Example XVIII 0.75 Parts of a sodium hydride dispersion 50% were suspended twice in 14 parts of petroleumether and the latter was decanted each time. The residue was suspended in 9 parts of N,N-dimethylformamide and added at once to a stirred solution of 7.35 parts of 6-[2-[4-[(4-fluorophenyl)-(4-hydroxyphenyl)methylene]-1-piperidinyl]ethyl]-3,7-dimethyl-5H-thiazolo[3,2-a]pyrimidin-5-one in 45 parts of N,N-dimethylformamide. The whole was heated to 45° C. and stirring was continued for 30 minutes at 45° C. After cooling to 25° C., 2.13 parts of iodomethane were added at once (exothermic reaction: temp. rose to 30° C.). Stirring was continued for 1 hour at room temperature. The reaction mixture was poured onto 300 parts of ice-water. The precipitated product was filtered off and dissolved in 240 parts of 4-methyl-2-pentanone. The organic phase was washed with 100 parts of water, dried, filtered and evaporated. The solid residue was suspended in 40 parts of acetonitrile. The product was filtered off and crystallized from 40 parts of acetonitrile. After cooling to 0° C., the product was filtered off and dried, yielding 3 parts (40%) of 6-[2-[4-[(4-fluorophenyl)(4-methoxyphenyl)methylene]-1-piperidinyl]ethyl]-3,7-dimethyl-5H-thiazolo[3,2-a]pyrimidin-5-one; mp. 140.2° C. (compound 142)

In a similar manner there were also prepared:

3-[2-[4-[(4-fluorophenyl)(4-methoxyphenyl)methylene]-1-piperidinyl]ethyl]-2-methyl-4H-pyrido[1,2-a]pyrimidin-4-one dihydrochloride.monohydrate; mp. 257.7° C. (compound 143);

6-[2-[4-[(4-fluorophenyl)(4-methoxyphenyl)methylene]-1-piperidinyl]ethyl]-7-methyl-5H-thiazolo[3,2-a]pyrimidin-5-one monohydrochloride; mp. 165.7° C. (compound 144);

7-[2-[4-[(4-fluorophenyl)(4-methoxyphenyl)methylene]-1-piperidinyl]ethyl]-3,4-dihydro-8-methyl-2H,6H-pyrimido[2,1-b][1,3]thiazin-6-one dihydrochloride; mp. 271.1° C. (compound 145); and 3-[2-[4-[(4-fluorophenyl)(4-methoxyphenyl)methylene]-1-piperidinyl]ethyl]-6,7,8,9-tetrahydro-2-methyl-4H-pyrido[1,2-a]pyrimidin-4-one dihydrochloride; mp. 268.5° C. (compound 146).

Example XIX

A mixture of 4 parts of 6-[2-[4-[bis(4-fluorophenyl)methylene]-1-piperidinyl]ethyl]-7-methyl-5H-thiazolo[3,2-a]pyrimidin-5-one, 1.3 parts of (+)-[R-(R*,R*)]-2,3-dihydroxybutanedioic acid and 96 parts of 2-propanol was stirred and heated till all solid entered solution. The whole was cooled while stirring. The product was filtered off and dried, yielding 5.1 parts (98%) of (+)-6-[2-[4-[bis(4-fluorophenyl)methylene]-1-piperidinyl]ethyl]-7-methyl-5H-thiazolo[3,2-a]pyrimidin-5-one [R-(R*,R*)]-2,3-dihydroxybutanedioate(1:1).; mp. 198.7° C. (compound 147).

Following an analogous salt-formation reaction there were also prepared:

3-[2-[4-[bis(4-fluorophenyl)methylene]-1-piperidinyl]ethyl]-2-methyl-4H-pyrido[1,2-a]pyrimidin-4-one sulfate(1:2).dihydrate; mp. 188.7° C. (compound 148);

3-[2-[4-[bis(4-fluorophenyl)methylene]-1-piperidinyl]ethyl]-2-methyl-4H-pyrido[1,2-a]pyrimidin-4-one (Z)-2-butenedioate; mp. 201.8° C. (compound 149);

3-[2-[4-[bis(4-fluorophenyl)methylene]-1-piperidinyl]ethyl]-2-methyl-4H-pyrido[1,2-a]pyrimidin-4-one 2-hydroxy-1,2,3-propanetricarboxylate(1:1); mp. 172.0° C. (compound 150);

6-[2-[4-[bis(4-fluorophenyl)methylene]-1-piperidinyl]ethyl]-7-methyl-5H-thiazolo[3,2-a]pyrimidin-5-one (Z)-2-butenedioate(1:1); mp. 180.3° C.; (compound 151);

6-[2-[4-[bis(4-fluorophenyl)methylene]-1-piperidinyl]ethyl]-7-methyl-5H-thiazolo[3,2-a]pyrimidin-5-one sulfate(1:2).monohydrate; mp. 178.6° C. (compound 152);

6-[2-[4-[bis(4-fluorophenyl)methylene]-1-piperidinyl]ethyl]-7-methyl-5H-thiazolo[3,2-a]pyrimidin-5-one 2-hydroxy-1,2,3-propanetricarboxylate(1:1).monohydrate; mp. 149.1° C. (compound 153);

6-[2-[4-[bis(4-fluorophenyl)methylene]-1-piperidinyl]ethyl]-7-methyl-5H-thiazolo[3,2-a]pyrimidin-5-one phosphate(1:2).monohydrate; mp. 150.6° C. (compound 154); and 6-[2-[4-[bis(4-fluorophenyl)methylene]-1-piperidinyl]ethyl]-7-methyl-5H-thiazolo[3,2-a]pyrimidin-5-one dihydrochloride; mp. 188.6° C. (compound 155).

Example XX

5 Parts of 3-[2-[4-[bis(4-fluorophenyl)methylene]-1-piperidinyl]ethyl]-2-methyl-4H-pyrido[1,2-a]pyrimidin-4-one dihydrochloride were dissolved in water and the base was liberated with ammonium hydroxide. The product was extracted with dichloromethane. The extract was dried, filtered and evaporated. The residue was stirred in a dilute ammonium hydroxide solution. The product was extracted wtih dichloromethane. The extract was dried, filtered and evaporated. The residue was crystallized from a mixture of 4-methyl-2-pentanone and 2,2'-oxybispropane. The product was filtered off and dried, yielding 2.2 parts of 3-[2-[4-[bis(4-fluorophenyl)methylene]-1-piperidinyl]ethyl]-2-methyl-4H-pyrido[1,2-a]pyrimidin-4-one; mp. 108.7° C. (compound 156).

What is claimed is:

1. A chemical compound having the formula

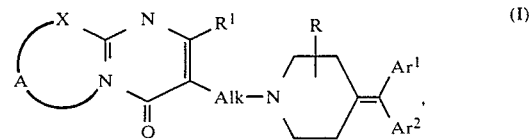

the possible stereochemically isomeric forms and the pharmaceutically acceptable acid-addition salts thereof, wherein:

R is hydrogen, hydroxy or lower alkyloxy;

$R^1$ is a member selected from the group consisting of hydrogen and lower alkyl;

Alk is a lower alkanediyl radical;

X is a member selected from the group consisting of —S—;

A is a bivalent radical having the formula —CH$_2$—CH$_2$—, —CH$_2$—CH$_2$—CH$_2$— or

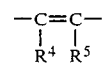

wherein $R^4$ and $R^5$ are each independently selected from the group consisting of hydrogen, halo, amino and lower alkyl; and Ar¹ and A² are each independently selected from the group consisting of pyridinyl, thienyl and phenyl, being optionally substituted with halo, hydroxy, lower alkyloxy, lower alkyl and trifluoromethyl.

2. A chemical compound according to claim 1 wherein Alk is an 1,2-ethanediyl radical.

3. A chemical compound according to claim 1 wherein the compound of formula (I) is 6-[2-[4-[bis(4-fluorophenyl)methylene]-1-piperidinyl]ethyl]-7-methyl-5H-thiazolo[3,2-a]pyrimidin-5-one or a pharmaceutically acceptable acid addition salt thereof.

4. A pharmaceutical composition in unit dosage form comprising per dosage unit a pharmaceutically acceptable carrier and an amount effective for treating patients suffering from psychosomatic disorders of at least one compound having the formula

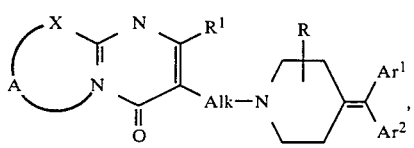

the possible stereochemically isomeric forms and the pharmaceutically acceptable acid-addition salts thereof, wherein:

R is hydrogen, hydroxy or lower alkyloxy;
R¹ is a member selected from the group consisting of hydrogen and lower alkyl;
Alk is a lower alkanediyl radical;
X is a member selected from the group consisting of —S—,
A is a bivalent radical having the formula —CH$_2$—CH$_2$—, —CH$_2$—CH$_2$—CH$_2$— or

wherein R⁴ and R⁵ are each independently selected from the group consisting of hydrogen, halo, amino and lower alkyl; and
Ar¹ and Ar² are each independently selected from the group consisting of pyridinyl, thienyl and phenyl, being optionally substituted with halo, hydroxy, lower alkyloxy, lower alkyl and trifluoromethyl.

5. A pharmaceutical composition according to claim 4 wherein Alk is an 1,2-ethanediyl radical.

6. A pharmaceutical composition according to claim 4 wherein the compound of formula (I) is 6-[2-[4-[bis(4-fluorophenyl)methylene]-1-piperidinyl]ethyl]-7-methyl-5H-thiazolo[3,2-a]-pyrimidin-5-one or a pharmaceutically acceptable acid addition salt thereof.

7. A method of treating patients suffering from psychosomatic disorders which comprises the systemic administration to said patients of a pharmaceutically acceptable amount of at least one compound having the formula

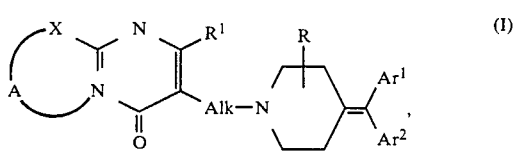

the possible stereochemically isomeric forms and the pharmaceutically acceptable acid-addition salts thereof, wherein:

R is hydrogen, hydroxy or lower alkyloxy;
R¹ is a member selected from the group consisting of hydrogen and lower alkyl;
Alk is a lower alkanediyl radical;
X is a member selected from the group consisting of —S—;
A is a bivalent radical having the formula —CH$_2$—CH$_2$—, —CH$_2$—CH$_2$—CH$_2$— or

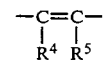

wherein R⁴ and R⁵ are each independently selected from the group consisting of hydrogen, halo, amino and lower alkyl; and
Ar¹ and Ar² are each independently selected from the group consisting of pyridinyl, thienyl and phenyl, being optionally substituted with halo, hydroxy, lower alkyloxy, lower alkyl and trifluoromethyl.

8. A method according to claim 7 wherein Alk is an 1,2-ethanediyl radical.

9. A method according to claim 7 wherein the compound of formula (I) is 6-[2-[4-[bis(4-fluorophenyl)methylene]-1-piperidinyl]ethyl]-7-methyl-5H-thiazolo[3,2-a]-pyrimidin-5-one or a pharmaceutically acceptable acid addition salt thereof.

* * * * *